United States Patent
Ducheyne et al.

(10) Patent No.: US 6,569,466 B2
(45) Date of Patent: May 27, 2003

(54) CONDITIONING OF BIOACTIVE GLASS SURFACES IN PROTEIN CONTAINING SOLUTIONS

(75) Inventors: Paul Ducheyne, Rosemont, PA (US); Shulamith Radin, Voorhees, NJ (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/793,453

(22) Filed: Feb. 26, 2001

(65) Prior Publication Data

US 2001/0014355 A1 Aug. 16, 2001

Related U.S. Application Data

(60) Division of application No. 08/977,093, filed on Nov. 24, 1997, now Pat. No. 6,224,913, which is a continuation-in-part of application No. 08/647,171, filed on May 9, 1996.

(51) Int. Cl.[7] .............................................. A61K 33/42
(52) U.S. Cl. .................. 424/602; 424/484; 424/489; 424/491; 424/494; 424/531; 424/724; 428/404; 523/212; 523/219; 604/891; 623/16
(58) Field of Search ................................. 523/218, 219; 428/404; 424/484, 489, 602, 724, 523, 531, 491, 494; 623/16–23; 604/890.1, 891

(56) References Cited

U.S. PATENT DOCUMENTS

| | | | |
|---|---|---|---|
| 3,960,583 A | 6/1976 | Netting et al. | 106/122 |
| 4,293,540 A | 10/1981 | Shikita et al. | 424/489 |
| 4,340,642 A | 7/1982 | Netting et al. | 428/402 |
| 4,411,847 A | 10/1983 | Netting et al. | 264/7 |
| 4,657,810 A | 4/1987 | Douden et al. | 428/313.9 |
| 4,737,411 A | 4/1988 | Graves, Jr. et al. | 428/403 |
| 4,842,863 A | 6/1989 | Nishimura et al. | 424/438 |
| 5,002,890 A | 3/1991 | Morrison | 435/286 |
| 5,024,826 A | 6/1991 | Linton | 423/335 |
| 5,055,307 A | 10/1991 | Tsuru et al. | 424/493 |
| 5,129,905 A | 7/1992 | Constantz | 606/76 |
| 5,204,106 A | 4/1993 | Schepers et al. | 424/423 |
| 5,328,955 A | 7/1994 | Rhee et al. | 525/54.1 |
| 5,356,617 A | 10/1994 | Schlossman | 424/63 |
| 5,480,844 A | 1/1996 | Matsui et al. | 501/3 |
| 5,591,453 A | 1/1997 | Ducheyne et al. | 424/484 |
| 5,593,680 A | 1/1997 | Bara et al. | 424/401 |
| 5,643,789 A | 7/1997 | Ducheyne et al. | 435/402 |
| 5,648,097 A * | 7/1997 | Nuwayser | 424/489 |
| 5,658,332 A | 8/1997 | Ducheyne et al. | 623/16 |
| 5,830,480 A | 11/1998 | Ducheyne et al. | 424/400 |

FOREIGN PATENT DOCUMENTS

WO  WO 00/44681  8/2000

OTHER PUBLICATIONS

El–Ghannam et al., "Formation of surface reaction products on bioactive glass and their effects on the expression of the osteoblastic phenotype and the deposition of mineralized extracellular matrix", *Biomat.*, 1997, 18, 295–303.

Li et al., "Effects of Ions in Aqueous Media on Hydroxyapatite Induction by Silica gel and its Relevance to Bioactivity of Bioactive Glasses and Glass–Ceramics", *J. Appl. Biomater.*, 1993, 4, 221–229.

(List continued on next page.)

*Primary Examiner*—Neil S. Levy
(74) *Attorney, Agent, or Firm*—Woodcock Washburn LLP

(57) ABSTRACT

Conditioning of the surface of silica-based glass or ceramic by differential immersion in a serum protein-containing solution, and the resultant microporous Ca-P surface layer having serum-protein like organic molecules, as defined herein intermingled throughout, is described.

16 Claims, 21 Drawing Sheets

OTHER PUBLICATIONS

Li et al., "Apatite Formation Inducted by Silica Gel in a Simulated Body Fluid", *J. Amer. Ceram Soc.*, 1993, 75(8), 2094–2097.

Mei et al (Abstract) *Bio Ceram. Proc. Int. Symp. Ceram. Med.*, 1993, 6, 67–72.

Pereira et al., "Calcium phosphate formation on sol–gel–derived bioactive glasses *in vitro*", *J. Biomed. Mat. Res.*, 1994, 28, 693–698.

Rohanizadeh et al., "Apatite precipitation in biphasic calcium phosphate ceramic after implantation: influence of implantation site", *Bioceramics*, 1997, 10, 27–30.

Radin, S. et al., "The effect in in vitro modeling conditions on the surface reactions of bioactive glass", *In Vitro Modeling Conditions of Bioactive Glass*, John Wiley & Sons, Inc., 1997, 363–375.

Radin, S. et al., "Transformation of Bioactive Glass Granules into CA–P Shells in Vitro", *Bioceramics*, 1997, 10, 45–48.

Radin, S. et al., "The Effect of Composition and In Vitro Immersion on the Formation of a Bioactive Surface on Sol–Gel Derived Glass", 23rd Annual Meeting of the *Society for Biomaterials*, Apr. 30–May 4, 1997, New Orleans, LA, 1 page.

Radin, S. et al., "Sol–Gel–Derived Glass (SG) with a Controlled Surface Reactivity", 23rd Annual Meeting of the *Society for Biomaterials*, Apr. 30–May 4, 1997, New Orleans, LA, 1 page.

Radin, S. et al. (Abstract) *Bio Ceram., Proc. Symp. Ceram. Med.*, 1993, 6, 59–65.

Schwarz et al., "Growth–promoting Effects of Silicon in Rats", *Nature*, 1972, 239, 333–334.

Yamamura et al. (Abstract) *J. Biomed.Mater.Res.*, 1992, 26(8), 1053–1064.

Ayyaswamy et al. (Invests.), Executive Summary and Research Project Description of invention, Sep. 1995, 27 pages.

Ducheyne, P., "Bioglass Coatings and Bioglass Composites as Implant Materials", *J. Biomed. Mat. Res.*, 1985, 19, 273–291.

Ducheyne, P., "The Use of Bioactive Glass Particles as Microcarriers in Microgravity Evironment", *Microgravity Science & Applications*: Program Tasks and Bibliography for FY 1995, NASA Technical Memorandum 4735, 1996.

Heinoken et al, "A New and Convenient Colorimetric Determination of Inorganic Orthophosphate and its Application to the Assay of Inorganic Pyrophosphate", *Anal. Biochem.*, 1981, 113, 313–317.

Iler, R.K., *The Chemistry of Silica: Solubility, Polymerization, Colloid and Surface Properties, and Biochemistry*, Wiley, New York, 1979.

O'Connor et al., "The Kinetics for the Solution of Silica in Aqueous Solutions", *J. Phys. Chem.*, 1958, 62, 1195–1198.

Schepers et al., "Bioactive Glass Particles of Narrow Size Range: An new Material for the Repair of Bone Defects", *Implant Dentistry*, 1993, 2(3), 151–156.

Brink, M., "The influence of alkali and alkaline earths on the working range for bioactive glasses", *J. Biomed. Mat. Res.*, 1997, 36, 109–117.

Carlisle, E.M., "Silicon as an essential trace element in animal nutrition", *Ciba Foundation Symposium*, 1986, 121, 123–139.

Carlisle, E.M., "Silicon: A Possible Factor in Bone Calcification", *Science*, 1970, 167, 279–280.

Carlisle, E.M., "Silicon: An Essential Element for the Chick", *Science*, 1972, 178, 619–621.

El–Ghannam et al., "Bioactive material template for in vitro synthesis of bone", *J. Biomed. Mat. Res.*, 1995, 29, 359–370.

Ishii et al., JP07157439, HCAPLUS, 1995, Abstract No. 773241.

NGK, JP 59/01145, 1984, Abstract No. 180011.

Mitsubishi, JP60106459, HCAPLUS, 1985, Abstract No. 583602.

Susama et al., *Chem. Concr. Res.*, 1995, 25(b), pp. 1305–1310.

Drenert: DE 4222763, 1/94.

Yoshiko et al., JP 62–158485, 7/87.

Paul et al., *J. Mat. Sci. Lett.*, 1995, 14(24), pp. 1792–1794.

* cited by examiner

US 6,569,466 B2

CONDITIONING OF BIOACTIVE GLASS SURFACES IN PROTEIN CONTAINING SOLUTIONS

REFERENCE TO RELATED APPLICATIONS

This application is a divisional of application Ser. No. 08/977,093, filed Nov. 24, 1997, now U.S. Pat. No. 6,224,913, which is a continuation-in-part of application Ser. No. 08/647,171, filed May 9, 1996, now U.S. Pat. No. 6,416,774, which is incorporated herein by reference in its entirety.

GOVERNMENT RIGHTS

The United States Government has a paid-up license in this invention and the right in limited circumstances to require that the patent owner license others on reasonable terms as provided for by the terms of NSF Grant No. BCS 93-09053 and NIH Grant No. DE-10693.

FIELD OF THE INVENTION

This invention relates to materials comprising silica-based glass or ceramic compositions having been treated to form a microporous calcium-phosphate (Ca-P) surface layer having serum-protein like organic molecules, as defined herein, intermingled throughout and, optionally, other biologically active molecules intermingled throughout and/or adsorbed thereon.

BACKGROUND OF THE INVENTION

In U.S. Pat. No. 5,204,106, issued to Schepers et al., (hereby incorporated by reference) the implantation of bioactive glass granules having the composition: 45% $SiO_2$, 24.5% $Na_2O$, 24.5% CaO and 6% $P_2O_5$, and a size range of 280–425 µm in diameter into the jaw of beagle dogs is disclosed. With particles of this size range, internal pouches formed in each of the particles and, subsequently, osteoprogenitor cells differentiated into osteoblasts within the pouches, actively laying down bone tissue. Next, bone tissue proliferated from the excavations, surrounded the particles and connected with bone tissue being formed around neighboring particles. Bone tissue was formed within the particle, without being bridged to the lingual or buccal bone plates. At 3 months, bone had grown throughout the surgical defects treated with glass granules. A similar phenomenon was not observed with particles of a larger size range, i.e., ~480–800 micrometers, or a smaller size range, i.e., ~210–300 micrometers.

Glass granules of narrow size range (300–360 µm) were used in a clinical trial in humans. Schepers et al., "Bioactive Glass Particles of Narrow Size Range: A New Material for the Repair of Bone Defects," *Inplant Dentistry*, 2(3): 151–156, 1993, incorporated herein by reference. In this clinical study, 87 patients and 106 maxillo facial defects were treated. At 3 months, the application sites had fully solidified. At six months, no radiological difference between the defect sites and the surrounding bone could be discerned.

It was subsequently discovered that particles in the size range 200–300 micrometers effected the same results if implanted into sites exhibiting a reduced metabolic state, particularly as compared to the maxillo-facial sites. Such sites are found, for example, in the appendicular skeleton, and in certain disease states. U.S. application Ser. No. 08/268,510, hereby incorporated by reference.

The in vivo event which initiates the reactions leading to the formation of bone throughout the defects is an excavation of the particles. The excavation is the result of physico-chemical reactions taking place in the glass, as well as a cell-mediated resorption of the internal reaction layer. Bioactive glass reacts at its surface with the formation of two reaction layers: a silica gel below the surface and a Ca-P rich layer at the surface.

It has now been discovered that differential immersion of other geometric forms of melt- or sol-gel-derived silica-based glass or ceramic in aqueous solutions containing serum-protein like organic molecules, as defined herein, results in a microporous surface layer of Ca-P having the serum-protein like organic molecules intermingled throughout. It is expected that silica-based glass or ceramic so conditioned will have an improved performance in vitro and in vivo, e.g., in relation to cell phenotype expression and attachment of cells in general. Prior treatments did not achieve this surface layer.

SUMMARY OF THE INVENTION

According to the present invention, silica-based glasses or ceramics are conditioned to achieve a microporous Ca-P surface layer having serum-protein like organic molecules, as defined herein, intermingled throughout and, optionally, biologically active molecules intermingled throughout and/or adsorbed thereon.

In one aspect, the present invention relates to a method for modifying the surface of silica-based glasses or ceramics by differential immersion in aqueous solutions containing serum-protein like organic molecules to achieve a microporous Ca-P surface layer having serum-protein like organic molecules intermingled throughout.

In yet another aspect, the present invention relates to a material comprising silica-based glasses or ceramics having a microporous Ca-P surface having serum-protein like organic molecules herein intermingled throughout, prepared by differential immersion of the silica-based glasses or ceramics in aqueous solutions containing serum-protein like organic molecules.

In a further aspect, the present invention relates to a material comprising silica-based glasses or ceramics having a microporous Ca-P surface layer having serum-protein like organic molecules intermingled throughout.

DETAILED DESCRIPTION

Figure 1A:
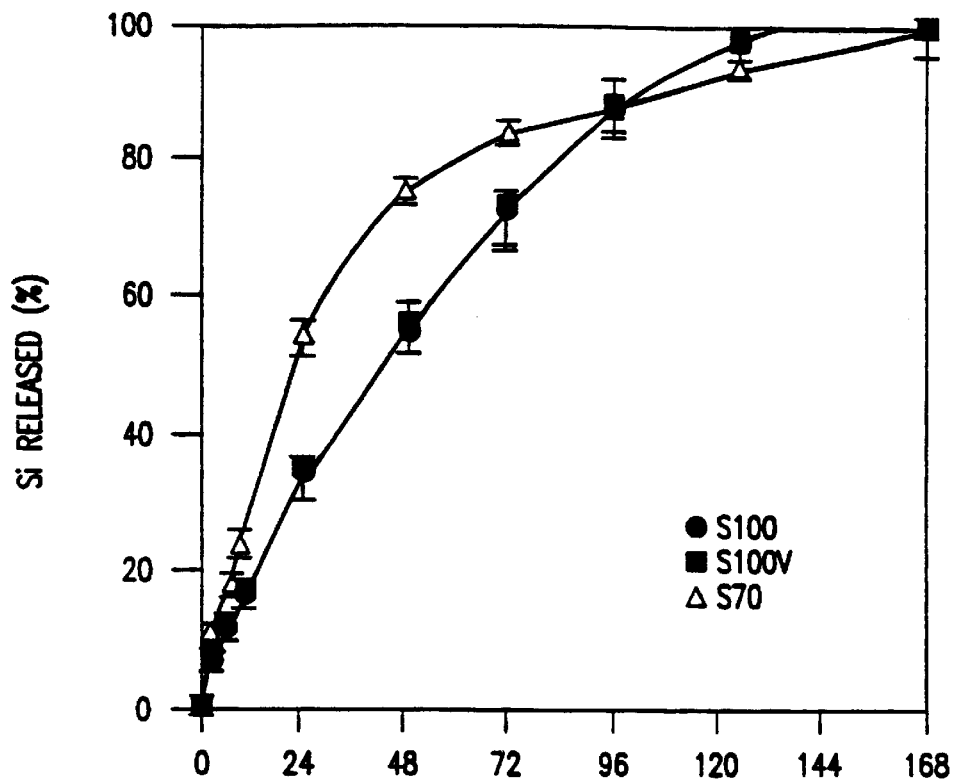
FIGS. 1a–c depict the changes in Si, Ca, and P content, respectively, during immersion of sol-gel derived particles as a function of glass composition.

The materials treated according to the present invention can be used in a variety of applications including, without limitation, to fill bony defects in sites present throughout the body of vertebrates for stimulating growth and repair. The materials can be used for the in vitro growth of bone and other tissues. The materials can also be used in vitro or in vivo with anchorage dependent cells or at sites with such cells. The materials are formed as a result of conditioning silica-based glass materials containing calcium and phosphate in vitro.

As used herein, "silica-based" refers to the inclusion of a silicon oxide in the composition of the glass. Other oxides may also be present.

"Bioactive" as used herein refers to a bone bioactive material having a calcium phosphate rich layer present, or which develops during appropriate in vitro or in vivo conditions. As observed by Pereira et al., J. of Biomed. Mat. Res., (1994) 28:693–698 (incorporated herein by reference), pure silica gel having a porous hydrated layer is able to induce a carbonated hydroxyapatite layer when soaked in a simulated body fluid containing calcium and phosphate ions. Pure silica hydrogels produced using TEOS and drying temperatures of around 400° C. were immersed in simulated body fluids having different magnesium, calcium, and phosphate ions. It was reported that apatite nucleation induction periods were decreased with the addition of small amounts of calcium and phosphate ions to the fluids, as well as increase in pH. Li et al., J. Appl. Biomater., (1993) 4:221–229 and Li et al., J. Amer. Ceram. Soc., (1993) 75:2094–2097 (both incorporated herein by reference).

Melt-derived silica-based, calcium and phosphate containing materials to be conditioned according to the present invention can be prepared following, for example, the procedure disclosed in U.S. Pat. No. 5,204,106, hereby incorporated by reference. The composition for the melt-derived glass can be as follows (in weight percent): $SiO_2$— 40–60; $Na_2O$ — 10–32 CaO— 10–32 and $P_2O_5$— 0–12. The composition for the melt-derived glass can also be $SiO_2$— 39–70; $Na_2$— 0–25; CaO— 8–20; and $P_2O_5$— 0–6. Brink, Maria, J. Biomed. Mat. Res., 36: 109–117, 1997, incorporated herein by reference. Other compounds, and oxides, may also be present, such as described in P. Ducheyne, "Bioglass coatings and bioglass composites as implant materials," J. Biomed. Mat. Res., 19:273–291, 1985, incorporated herein by reference.

The sol-gel derived materials can be prepared following, for example, the procedures disclosed in U.S. Pat. No. 5,591,453, hereby incorporated by reference. The compositional range for the sol-gel derived glass can be as follows (in weight percent): $SiO_2$— 60–100; CaO— 0–40; and $P_2O_5$— 0–10.

The in vitro excavation of the silica-based, Ca-P containing glass granules and transformation into Ca-P shells disclosed in prior application Ser. No. 08/647,171 was achieved by differential immersion of the glass granules in, inter alia, serum-containing solutions which provoked the dissolution of silicon from the glass matrix. Similar conditioning can be applied to other geometric forms of melt- and sol-gel-derived bioactive glasses, including, but not limited to, disks, blocks, monoliths, fibers, coatings, and rods, resulting in a novel surface. Differential immersion can be achieved by periodic solution exchange in a system in which the solution is static, or by use of a dynamic system in which the immersion solution is continuously supplied as a flow of fresh solution. See, U.S. Pat. No. 5,002,890, issued to Dennis R. Morrison on Mar. 26, 1991 for an example of how to achieve dynamic fluid replenishment in, that case, tissue culture.

The immersion conditions such as, for example, solution composition, duration, number of solution exchanges, material weight to solution volume ratio (W/V), can vary to a great degree as long as the formation of the calcium phosphate layer is perpetuated. The appropriate conditions to achieve the invention described herein can be readily determined by one skilled in the art.

The immersion conditions for the in vitro excavation were previously selected to allow the following events to occur: 1) formation of a surface Ca-P layer; and 2) continuous dissolution of the silica-network, remaining under the Ca-P layer, until about 80 to 100% of the original Si content in the glass is dissolved. In order to stimulate the continuous silica network dissolution, the solution used for the immersion must remain undersaturated with respect to soluble silica. Events 1) and 2) can be achieved by consecutively different solutions. For example, in the case of a glass composed of 100% silica, a calcium-phosphate surface layer must first be formed. This can be accomplished by immersing the glass in solutions saturated in silicon, such as described in U.S. application Ser. No. 08/647,007 (our docket UPN-2745), hereby incorporated by reference.

The immersion conditions for conditioning the silica-based glass and ceramics according to the present invention are similar. The exchange of solution perpetuates the formation of the microporous Ca-P surface layer having serum-protein like organic molecules, as defined herein, intimately intermingled throughout.

Once this microporous Ca-P surface layer is formed, subsequent immersions can be performed in aqueous solutions containing other biologically active molecules, with or without the serum-protein like organic molecules, as defined herein, present. The subsequent immersions can be performed in an integral mode, as defined herein, and are performed for a time sufficient to allow adsorption of the biologically active molecules onto the surface of the microporous Ca-P surface layer, including within the pores. For example, immersion times of from about 5 minutes to about 160 hours are contemplated.

The following reactions are involved in the transformation of the melt-derived glass: hydrolysis and formation of a silica-gel layer; migration of Ca and $PO_4$ ions from the bulk through the Si-gel to the surface; accumulation of the ions at the surface and formation of a Ca-P rich surface; continuous growth of the Si-gel and Ca-P rich layers; and continuous silica dissolution.

The following reactions are involved in the transformation of sol-gel derived glass granules: loss of soluble silica along with migration of Ca and $PO_4$ ions through highly porous glass to the surface; leaching of the ions to a solution along with partial accumulation at the surface; formation of a CaP- surface layer; growth of the CaP-layer along with continuous silica dissolution.

Some aqueous solutions which can be used include, but are not limited to, the following:

a) water;

b) ion-free, Tris buffer, with an initial pH of from about 6.8 to about 8.0—for melt-derived bioactive glass;

c) phosphate buffer solution with an initial pH of from about 6.8 to about 8.0; and d) Tris or phosphate buffer solutions containing varying concentrations of Ca and $PO_4$ ($HPO_4$ or $H_2PO_4$) with or without addition of varying concentrations of other ions including, but not limited, to Na, K, Cl, $CO_3$, and Mg, or their combination.

Solution d) is used when the glass or ceramic is 100% silicon oxide. The immersion solution must also contain serum-protein like organic molecules, as defined herein, which result in the formation of a microporous Ca-P surface layer. The immersion solution can also contain biologically active molecules as define herein, and/or such molecules can be adsorbed after formation of the microporous Ca-P surface layer.

With increasing stability of the silica-based glass—such as increasing the amount of network former $SiO_2$, increasing the amount of network modifiers that render the network more stable (see Ducheyne, supra), or, in the case of melt-derived glass, replacing $Na_2O$ with a more stable alkali oxide—the duration of treatment and/or the number of solution exchanges will have to be increased, or the material size will have to be reduced. The presence of serum-protein like organic molecules in the immersion solution decreases the dissolution rate. A possible explanation is that the adsorption of the proteins on the surface of the glass modifies the surface of the glass in contact with solution.

The dissolution of various forms of solid silica in aqueous solutions has been the focus of several studies. O'Connor et al., "The kinetics for the solution of silica in aqueous solutions," *J. Phys. Chem.*, 62:1195–8, 1958; and Iler, R. K., *The Chemistry of Silica: Solubility. Polymerization, Colloid and Surface Properties, and Biochemistry*, Wiley, N.Y., 1979. It has been established that any form of solid silica in contact with aqueous solutions dissolves into monosilicic acid $Si(OH)_4$ until the solution reaches saturation. By exchanging the immersion solution such that saturation is never reached, the diffusion process is favored and thus dissolution is enhanced. The in vitro dissolution behavior during the differential immersion is expected to be similar to that observed in vivo, during which the body fluid is continuously replenished.

"Microporous Ca-P surface layer" as used herein refers to a surface layer containing calcium and phosphorous. Other compounds, for example, silicon, may also be present.

As used herein, the term "about" means approximately ±10%, except when referring to immersion times, in which case about means ±a day or two.

"Serum-protein like organic molecules", as defined herein, refers to organic molecules having the same effect as serum proteins following differential immersion of silica-based glass or ceramic therein, i.e., resulting in the formation of a microporous Ca-P surface layer. Serum-protein like organic molecules according to the present invention can be readily determined by those skilled in the art following the disclosure herein. Serum-protein like organic molecules produced by synthetic means, including genetic engineering, are included in the present invention, as are derivatives containing the active domains of said organic molecules, e.g., the binding domains of attachment molecules. When present during differential immersion, serum-protein like organic molecules slow down the Ca-P precipitation which protects the underlying glass network from degradation during dissolution. The Ca-P layer is also microporous and, thus, there is not sufficient protection of the underlying glass network, and dissolution of silicon and formation of a Ca-P layer at the surface continues with solution replenishment. Combinations of serum-protein like organic molecules are also included.

The term "bony defect", as used herein, refers to regions necessitating growth or repair including, but not limited to, fractures, areas of erosion or degradation, osteolysis, holes resulting from removal of screws and pins, replacements, periodontal applications, and deterioration of bone due to old age or disease.

As used herein, "biologically active molecules" are defined as those organic molecules having an effect in a biological system, whether such system is in vitro, in vivo, or in situ. Biologically active molecules include, but are not limited to, the following categories: growth factors, cytokines, antibiotics, anti-inflammatory agents, analgesics and other drugs, and cell attachment molecules. It is contemplated that many serum-protein like organic molecules will also function as biologically active molecules, and vice versa.

The term "antibiotic" includes bactericidal, fungicidal, and infection-preventing drugs which are substantially water-soluble such as, for example, gentamicin, vancomycin, penicillin, and cephalosporins.

The term "growth factors" refers, without limitation, to factors affecting the function of cells such as osteogenic cells, fibroblasts, neural cells, endothelial cells, epithelial cells, keratinocytes, chondrocytes, myocytes, cells from joint ligaments, and cells from the nucleus pulposis. Platelet derived growth factors (PDGF), the transforming growth factors (TGF-β), insulin-like growth factors (IGFs), fibroblast growth factors (FGFs), and the bone morphogenetic proteins (BMPs) are examples of growth factors encompassed in the various geometric forms according to the present invention.

The term "cell attachment molecules" as used herein includes, but is not limited to, fibronectin, vitronectin, collagen type I, osteopontin, bone sialoprotein, thrombospondin, and fibrinogen. Such molecules are important in the attachment of anchorage-dependent cells to the tissue matrix or to implant materials.

The term "intermingled throughout" as used herein means that the molecules, e.g., serum-protein like organic molecules, as defined herein, are distributed throughout the microporous Ca-P surface layer and are not just adsorbed on or embedded in on its surface.

The term "microporous" as used herein refers to a pore size of from about 0.1 to about 10 μm.

The term "macroporous" as used herein refers to a pore size of from about 40 to about 1000 μm.

The term "dense" as used herein in reference to a glass or ceramic means substantially non-porous.

Previously, we proposed to treat the bioactive glass with a two step treatment (see U.S. Pat. No. 5,643,789). We treated bioactive glass because we found that creating a Ca-P surface on which proteins were adsorbed stimulated the expression of the osteoblast phenotype. However, the Ca-P layer which is created is relatively thin, in contrast to the layer one observes on bioactive glass after in vivo implantation. In addition, the Ca-P and protein are not mixed together as would be the case when the layer is formed in vivo. In this previously invented two-step conditioning treatment, the first step of the treatment is performed in protein-free medium and quickly leads to the formation of a protective Ca-P film which prevents the corrosion reactions from proceeding deeper and deeper into the material. Further, since the proteins are only adsorbed in a second step, the protein layer is adsorbed only on top of the Ca-P layer.

Immersing the bioactive glass in a solution containing serum without changing the solution during the immersion period—i.e., an integral immersion as the term is used herein—did not produce the desired composite organic-inorganic layer—i.e., a layer with intermingled Ca-P and serum-protein like organic molecules. Further, we found that the kinetics of the formation of the Ca-P surface reaction layers were extremely slow in comparison with its formation in an electrolyte solution without serum. Others before us had also used tissue culture solutions to study reaction layer formation on bioactive glasses.

In the present invention, we disclose a microporous Ca-P surface layer intermingled with serum-protein like organic molecules. Furthermore, this invention includes the methodology to obtain relatively thick Ca-P-serum-protein like organic molecule layers, which can be digested by cells. The thicker Ca-P-serum-protein like organic molecule layer for digestion by cells is expected to have a beneficial effect.

We propose that the carbonated hydroxyapatite layer typically observed on bioactive glass after implantation is formed as a result of activity of bone cells adhered onto the initial reaction layer. This reasoning follows from two sets of experiments in our laboratory. We showed that, prior to the formation of a carbonated hydroxyapatite layer, an amorphous Ca P layer, intermingled with Si, forms. Performing Fourier transform infrared spectroscopy on two sets of glass samples after identical experimental conditions except for the presence of neonatal rat calvaria osteoblasts, we also found either no evidence of carbonated hydroxyapatite (no cells present), or very clear evidence (with osteoblasts) (El-Ghannam et al., *J. Biomed. Mat. Res.*, 29: 359–370, 1995). Furthermore, using energy dispersive X-ray analysis, we measured significant differences in elemental concentration on one sample after two days of osteoblast culture between areas covered by extracellular matrix elaborated by the cells, and those areas not yet covered (El-Ghannam et al., *Biomat.*, 18:295–303 (1997). Prominent Ca, P and Si peaks were evident under the extracellular matrix. Areas not covered by matrix revealed small Si and P peaks and a pronounced Ca peak. Noteworthy, it is not just the interaction of the initial surface reaction layer with cells, but also the intriguing presence of Si in those areas where there is marked cellular activity.

Furthermore, having the serum-protein like organic molecules intermingled throughout the surface is expected to be beneficial as well. It has been previously reported that adsorbed, nonspecific proteins at a bone site are regularly eliminated from the ceramic surface due to cellular degradation (Rohanizadeh et al., *Bioceramics,* 10:27–30, 1997). Accordingly, a thick layer of Ca-P having proteins intermingled throughout will stimulate additional cellular activity.

We have now found that if we continuously replenish the immersion solution in which the surface reaction layer is formed, we perpetuate the reaction at the glass or ceramic surface and continue to form an increasingly thicker layer of microporous Ca-P intermingled with organic compounds of the immersion solution. Furthermore, the microporous Ca-P surface layer forms even when the glass or ceramic to be treated is not itself porous, i.e., is dense.

Replenishing the solution can be achieved by immersing the glass objects in a volume of solution in, for example, a vial or receptacle and exchanging the solution from time to time either through a partial or total solution exchange. Alternatively, the glass or ceramic to be surface-treated can also be placed in a system that permits continuous flow of the treatment solution past the glass surfaces, such as are discussed above.

The surface layers and the methods for making these are extremely useful in any application where cells make contact with the material by virtue of the stimulatory nature of the surfaces on cell function. By now having a surface that is a continuous mixture of Ca-P and serum-protein like organic molecules, there is a continual intra- and extra-cellular effect arising from both the chemical components of the mineral phase of bone as well as the serum-protein like organic molecules. This effect will greatly stimulate tissue engineering procedures in vitro and in vivo. Bone tissue engineering procedures will particularly benefit from these new and unexpected findings. Further, any anchorage dependent cell can be placed in contact with the newly developed surface reaction layer.

In our invention there is the added advantage that silicon is incorporated throughout the surface reaction layer in tandem with the serum-protein like organic molecules. No other treatment leads to the simulanteous incorporation of both. Data using our prior two-step treatment indicates the presence of prominent Si and P peaks, in addition to a Ca peak, only under extracellular matrix elaborated by osteoblast cells in culture on bioactive glass. El-Ghannam et al., *J. Biomed. Mat. Res.,* 29:359–370 (1995) and El-Ghannam et al., *Biomat.,* 18:295–303 (1997).

Others have suggested that silicon is associated with calcium in an early stage of bone formation. Carlisle found that silicon is required for normal growth and development in the chick. E. M. Carlisle, *Science,* 167:279–280 (1970) and E. M. Carlisle, *Science,* 178:619–621 (1972). Schwarz et al. reported that silicon deficiency in the rat resulted in depressed growth and skull formation. Schwarz et al., *Nature,* 239:333–334 (1972). Later, Carlisle reported that silicon's primary effect is on the matrix, i.e., that silicon is required for collagen and glycosaminoglycan formation. Carlisle also noted that additional support for silicon's metabolic role in connective tissue was provided by the finding that silicon is a major ion of osteogenic cells and is present in especially high concentrations in the metabolically active state of the cell and that, further, silicon reaches relatively high levels in the mitochondria of these cells. E. M. Carlisle, *Ciba Foundation Symposium,* 121:123–139 (1986).

As is disclosed below, the composition and morphology of the surface of the invention are different from that formed by immersion in a serum-free medium, followed by an immersion in serum. Using the method according to the invention, we found that the reaction surface comprises a microporous Ca-P surface layer having serum-protein like organic molecules, intermingled throughout. The surface layer formed in serum has a lower Ca/P ratio (about 1.2–1.3) than the surface formed in serum-free solutions (>1.45) and contains significant amounts of Si of which it was previously suggested to have an effect on bone cell function. The invention lies in the achievement of this reaction surface.

The method to create these beneficial reaction layers on silica-based glass or ceramic, e.g., bioactive glass, is typically as follows. The solution containing the serum-protein like organic molecules can comprise serum. The serum source can be, without limitation thereto, human, bovine, porcine, etc. Differential immersion (immersion with solution exchange at designated time periods) in serum-containing, buffered (pH 7–7.6) solutions such as Tris or phosphate buffered solution, either ion-free or containing ions similar to those found in human plasma. Serum content can vary from about 1% to about 100%, preferably from about 8% to about 100%. The total protein content in serum generally can vary from about 3.0% to about 9.0%. Accordingly, when the immersion solution does not comprise serum, concentrations of the serum-protein like organic molecules from about 0.03%, preferably about 0.08%, and greater can be used. The immersion solution can additionally contain other biologically active molecules, as defined herein, including but not limited to attachment molecules, growth factors, collagen, etc.

The total immersion time can vary from about 1 hour up to about two weeks. Depending on the desired surface composition and thickness of the reaction layer(s), and concentration of serum-protein like organic molecules, shorter or longer immersion times may be appropriate. The immersion times and conditions can be readily ascertained by persons of ordinary skill in the art. The differential immersion process involves either the continuous flow of solution past the treatment surface or the periodic replenishment of the solution. The solution is an aqueous medium (with or without electrolytes) supplemented with serum-protein like organic molecules, as defined herein.

The method can be performed upon melt- or sol-gel-derived dense or macroporous glass or ceramic with a similar result. The resultant surface has a microporous structure, e.g., having pore sizes from about 0.1 μm to about 10 μm of uniform pore size.

The immersion experiments reported herein demonstrate major differences between surface modification of bioactive glass by differential immersion in serum-containing solutions, in comparison to those which occur upon integral immersion in either serum-free or serum-containing solutions. The differential immersion in serum-containing solutions allows one to overlay a surface layer with unique properties, i.e. to create a microporous Ca-P surface layer having organic molecules intermingled throughout.

The microporous surface allows the elements of tissues to penetrate into the micropores upon implantation. Further, the porous structure facilitates a controlled release of molecules intermingled throughout and, optionally, adsorbed thereon in a subsequent treatment. Additionally, the pores provide a greater surface area for interaction with body fluids upon implantation.

Figure 7A:
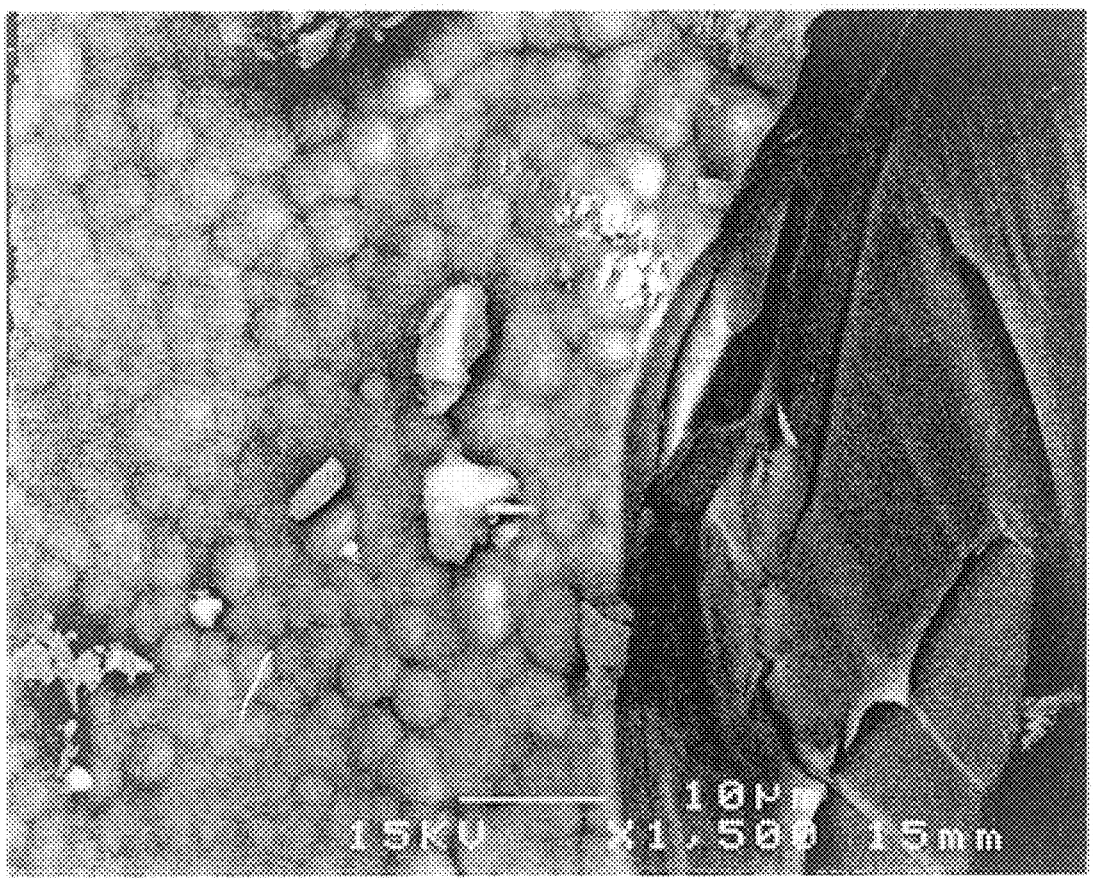
FIGS. 7a–c are SEM, EDXA, and FTIR, respectively, depicting the changes in morphology, composition and structure, respectively, of the surfaces following differential immersion in serum-free solution.
Figure 7B:
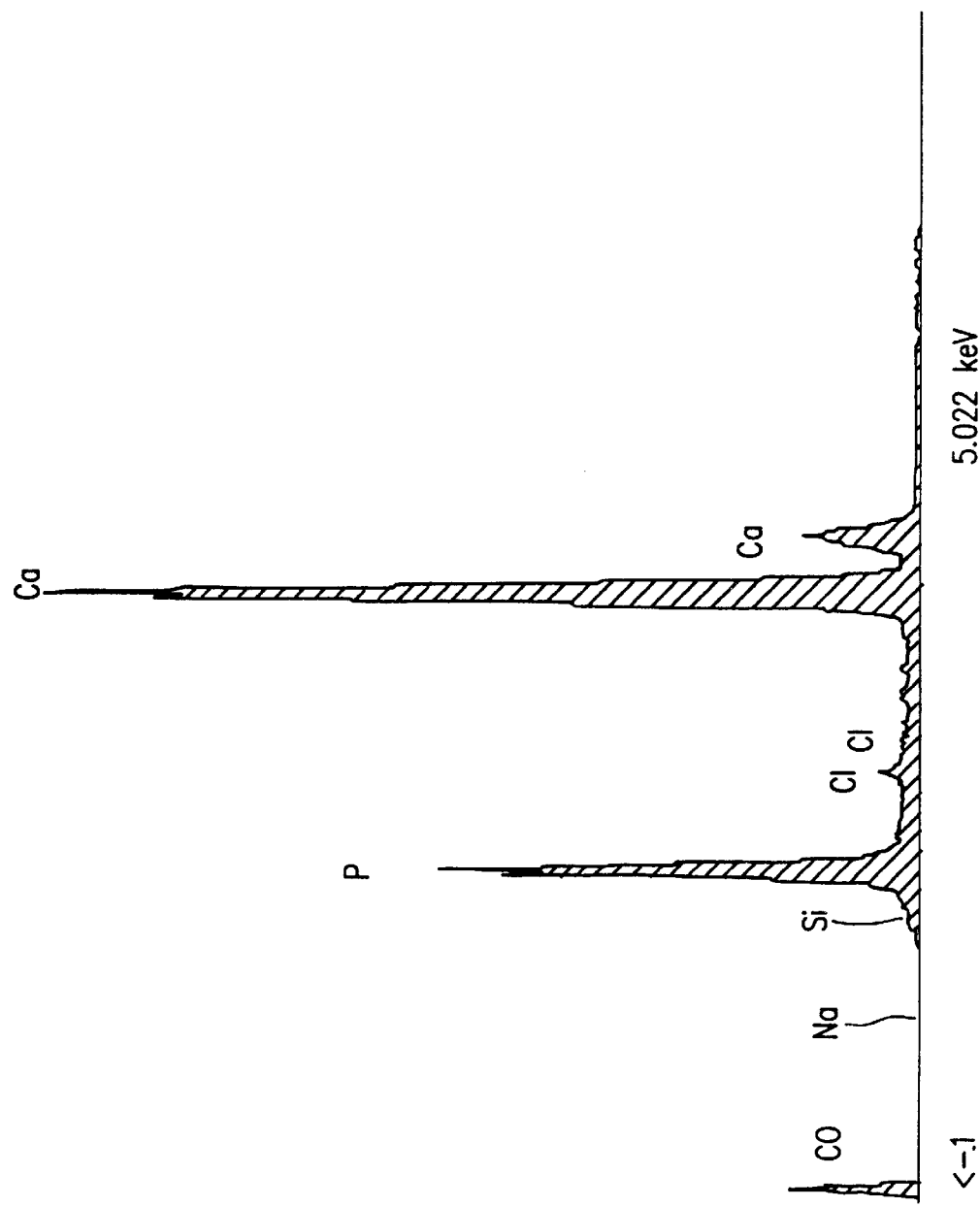
Figure 7C:
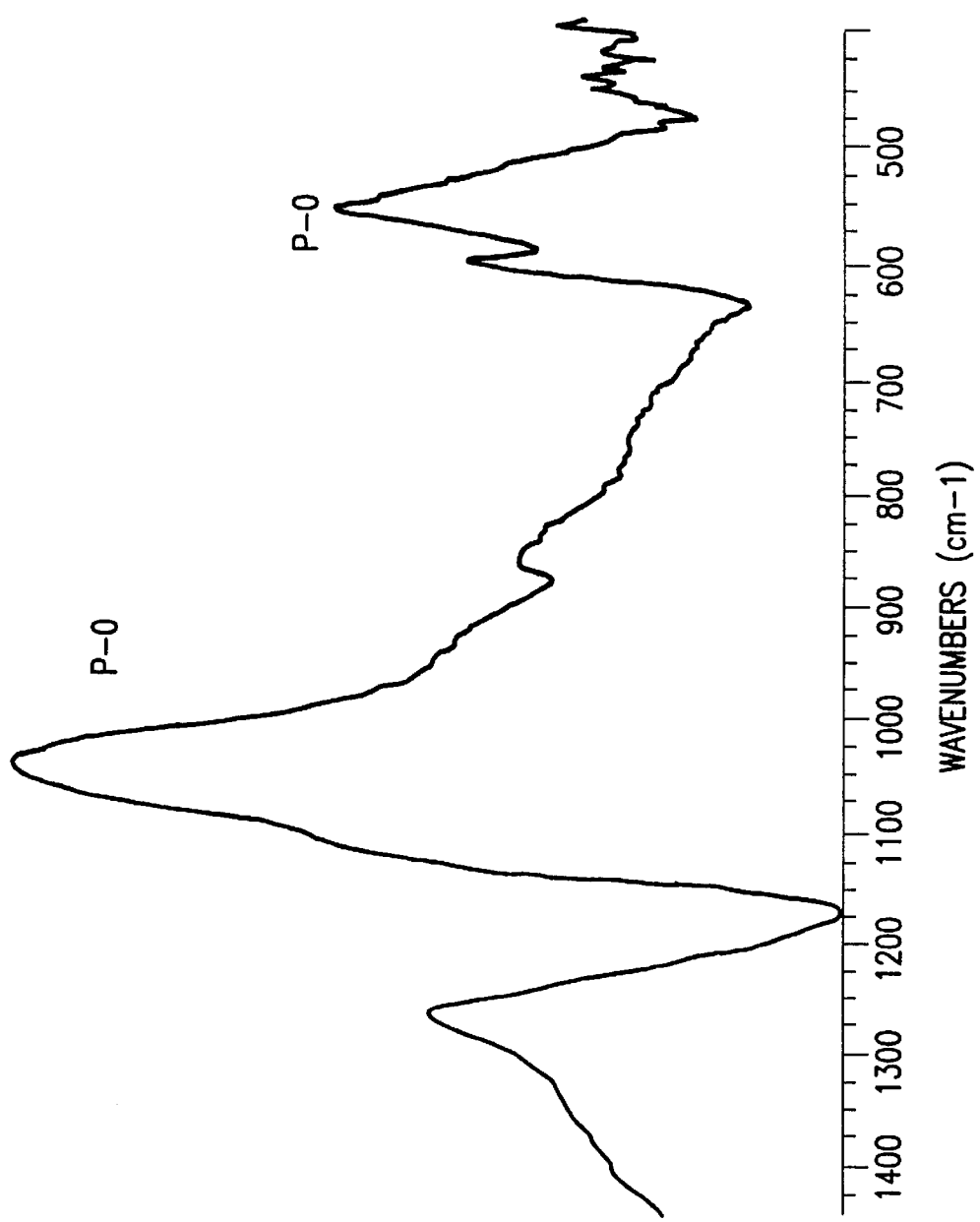
Figure 10A:
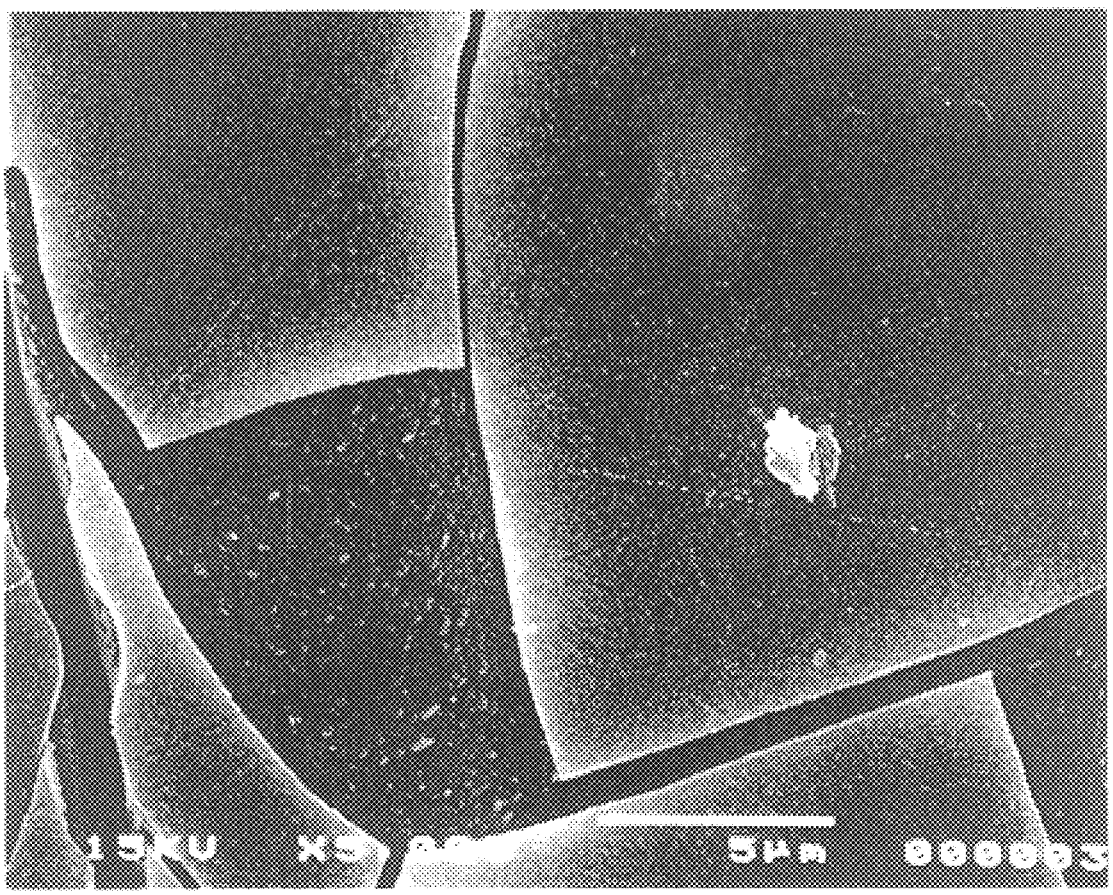
FIGS. 10a–d are SEM, EDXA (b and c), and FTIR, respectively, depicting the changes in morphology, composition, and structure, respectively, of the surfaces following integral immersion in serum-containing solution.
Figure 10B:
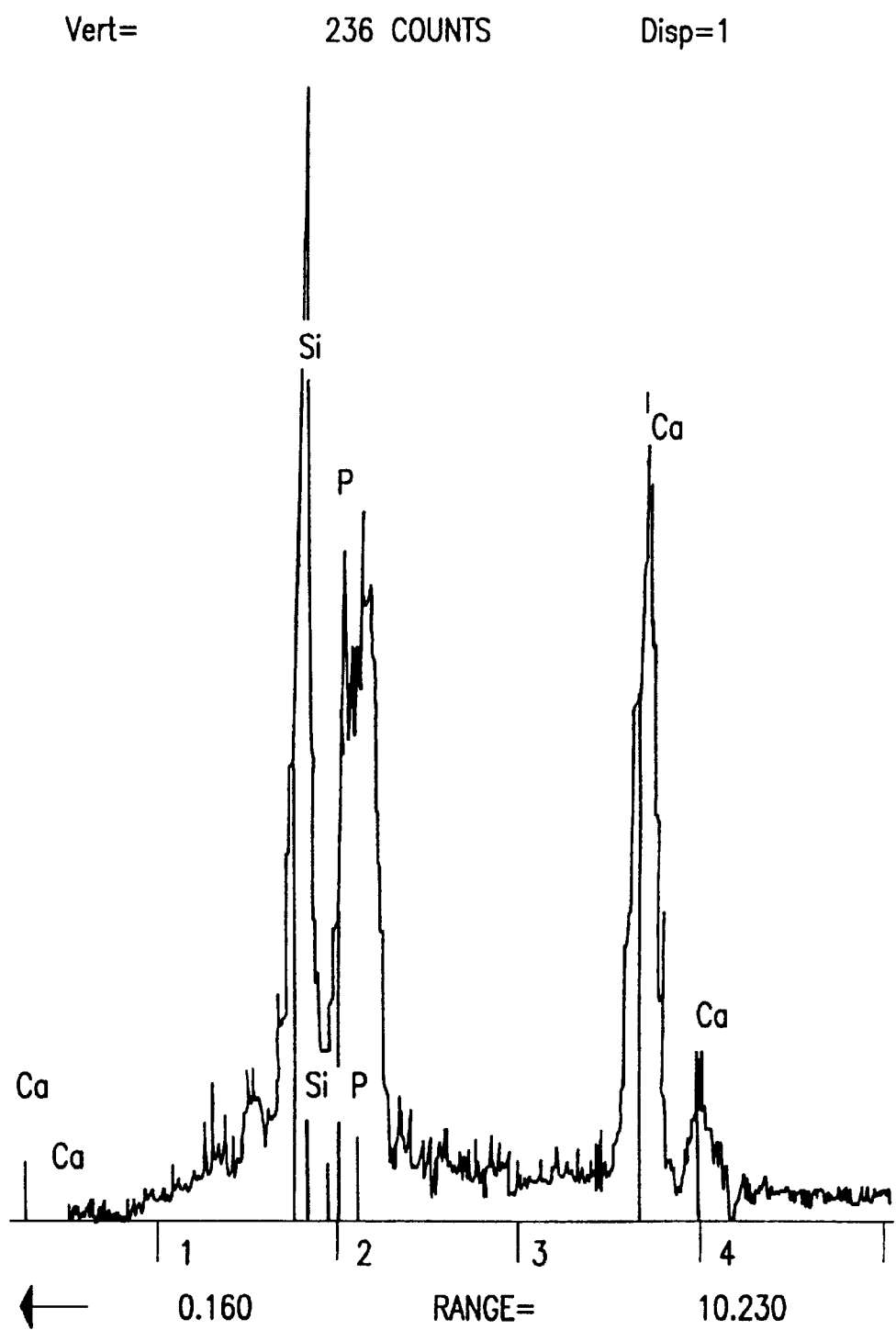
Figure 10C:
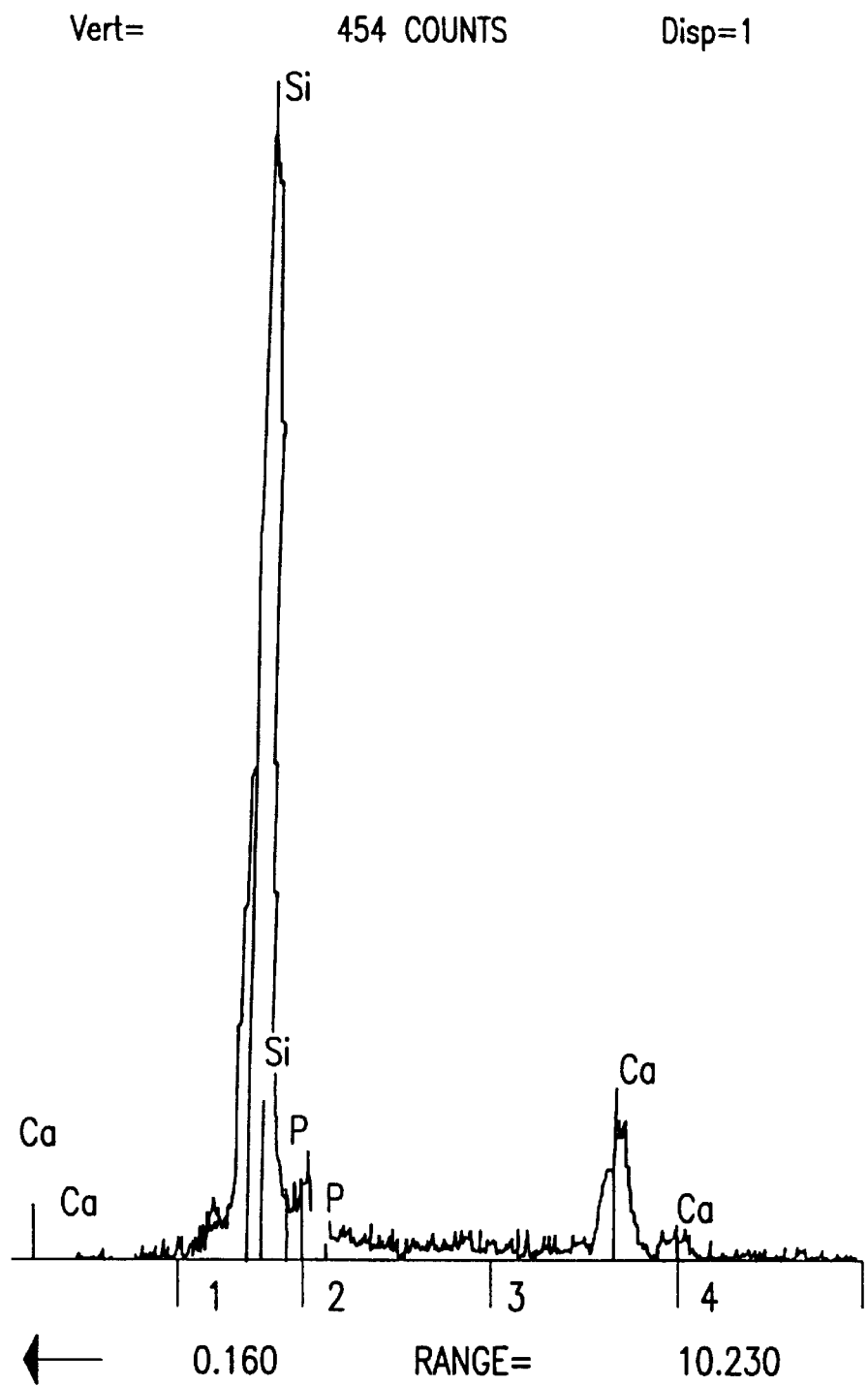
Figure 10D:
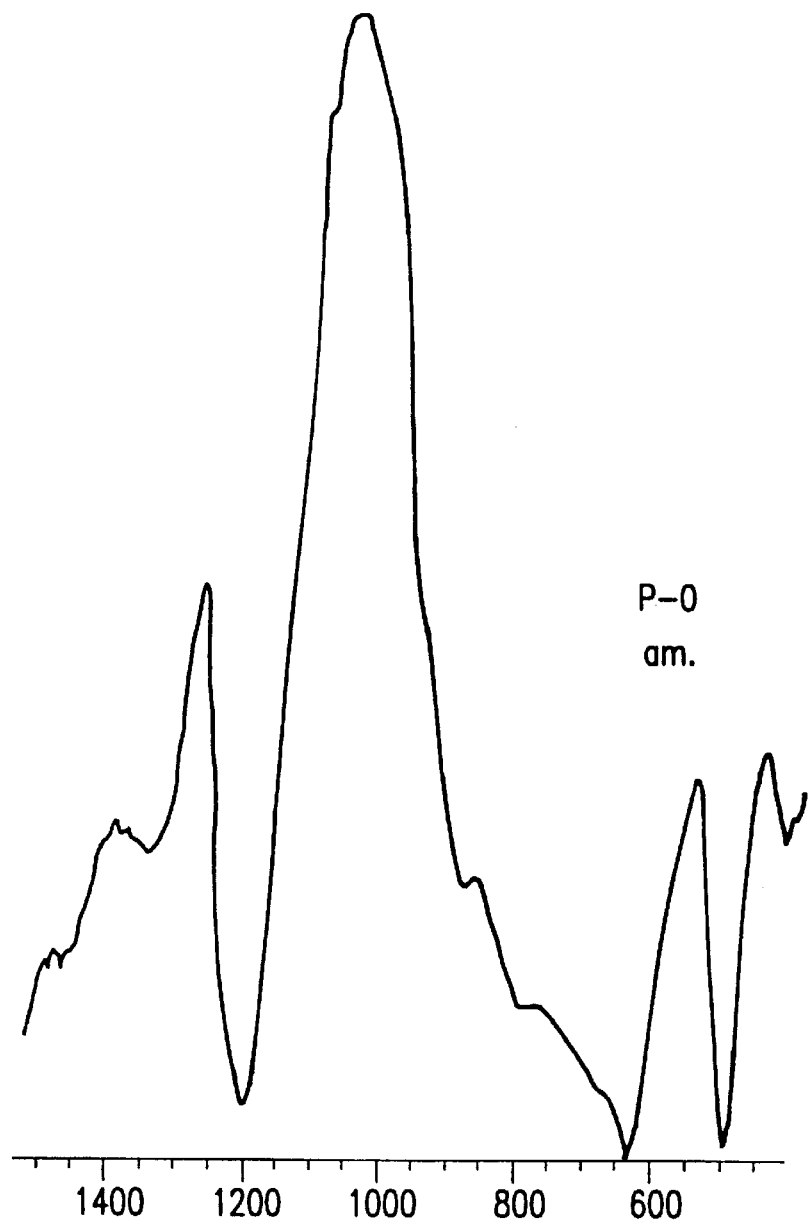

The differential immersion enhances formation of crystalline Ca-P phases with similar characteristics as the mineral phase of bone, particularly in comparison to the integral immersion in serum protein-containing solutions. Indeed, FTIR analysis showed formation of crystalline Ca-P phases after differential immersion (1 week) in serum-containing solution (FIG. 7c). In contrast, Ca-P phases present in the surface layer after integral immersion for the same time period were amorphous (FIG. 10d).

In comparison, integral immersion in serum protein-containing solutions created a smooth, dense, fragile and amorphous surface consisting of a silica layer and a silica matrix with accumulated calcium and phosphate.

In contrast to differential immersion in serum-containing solution, differential immersion in serum-free solution produced a dense surface layer composed of closely packed Ca-P precipitates which cannot be intermingled with proteins.

Example 1 below describes the excavation of particles using differential immersion under conditions similar to the present invention. An example of conditioning according to the present invention, with comparison to other conditioning methods, is provided in Example 2 below.

EXAMPLE 1

Transformation of sol-gel-derived glass 45S5 granules into hollow Ca-P shells using Differential Immersion Specimens prepared according to Example 1 of application Ser. No. 08/647,171 were immersed in three solutions: TE, TE supplemented with 10% serum (vol %), and 100% serum. Newborn calf serum was used. The solutions were chosen to address effect of important constituents of the in vivo milieu. Immersions were performed in vials. TE is a non-proteinaceous control that contains the electrolyte constituents of human blood plasma in similar concentrations (cf. Table I). TE was prepared by dissolving reagent grade NaCl, KCl, NaHCO$_3$, MgCl$_2$.6H$_2$O, MgSO$_4$.7H$_2$O, KHPO$_4$anh. and CaCl$_2$.2H$_2$O in a 0.05 M Tris [hydroxymethyl] aminomethane hydrochloride buffered solution. The resulting pH was 7.4 at 37° C.

TABLE I

Ionic content of human blood plasma and TE.

| Ion | Human blood plasma (mM) | TE (mM) |
|---|---|---|
| Ca$^{2+}$ | 2.5 | 2.5 |
| HPO$_4^{2-}$ | 1.0 | 1.0 |
| Na$^+$ | 142.0 | 152.0 |
| Cl$^-$ | 103.0 | 136.0 |
| K$^+$ | 5.0 | 5.0 |
| Mg$^{2+}$ | 1.5 | 1.5 |
| HCO$_3^-$ | 27.0 | 27.0 |
| SO$_4^{2-}$ | 0.5 | 0.5 |

A differential immersion was effected by exchange with fresh solution at various time points throughout the duration of immersion. In the present example, the samples were exposed to fresh solution after 3, 6, 9, 24, 48, 72, 96, 124 and 168 hours of immersion. These intervals were chosen in an attempt to maintain a maximum concentration of Si in solution less than ⅔ of the saturation concentration. The immersion protocol was intended to reflect the continuous replenishment of body fluid at the implant site. The samples were immersed for up to 7 days.

Three samples were tested per set of conditions. The weight to solution volume ratio was 0.5 mg/ml. The samples were placed in an incubator at 37° C. in a 5% CO$_2$ atmosphere and continuously shaken (200 revolutions/minute). The vials were loosely capped to minimize evaporation without preventing gas exchange.

The testing conditions (i.e.,sample, immersion mode, and solution) and the parameters studied are listed in Table II. Upon completion of the selected immersion protocols, the solutions were collected and the retrieved particles were rinsed with ethanol and dried in ambient air.

TABLE II

| | Testing conditions | |
|---|---|---|
| Composition | Particle size | Solution |
| S100 | 500–710 μm | TE |
| S100 V | | |
| S70 | | |
| S70 | 210–500 μm | TE |

TABLE II-continued

| | Testing conditions | |
|---|---|---|
| Composition | Particle size | Solution |
| S70 | 500–710 μm | TE |
| | | TE + 10% serum |
| | | serum |

The Si and Ca concentrations were measured by flame atomic absorption spectrophotometry (FAAS, Perkin-Elmer 5100PC). The P concentration was determined using a colorimetric method (Heinoken et al., "A new and convenient colorimetric determination of inorganic orthophosphate and its application to the assay of inorganic pyrophosphate," *Anal. Biochemistry*, 113:313–7, 1981,) (Molybdenum yellow) (Pharmacia LKB Ultrospec Plus Spectrophotometer).

Figure 1B:
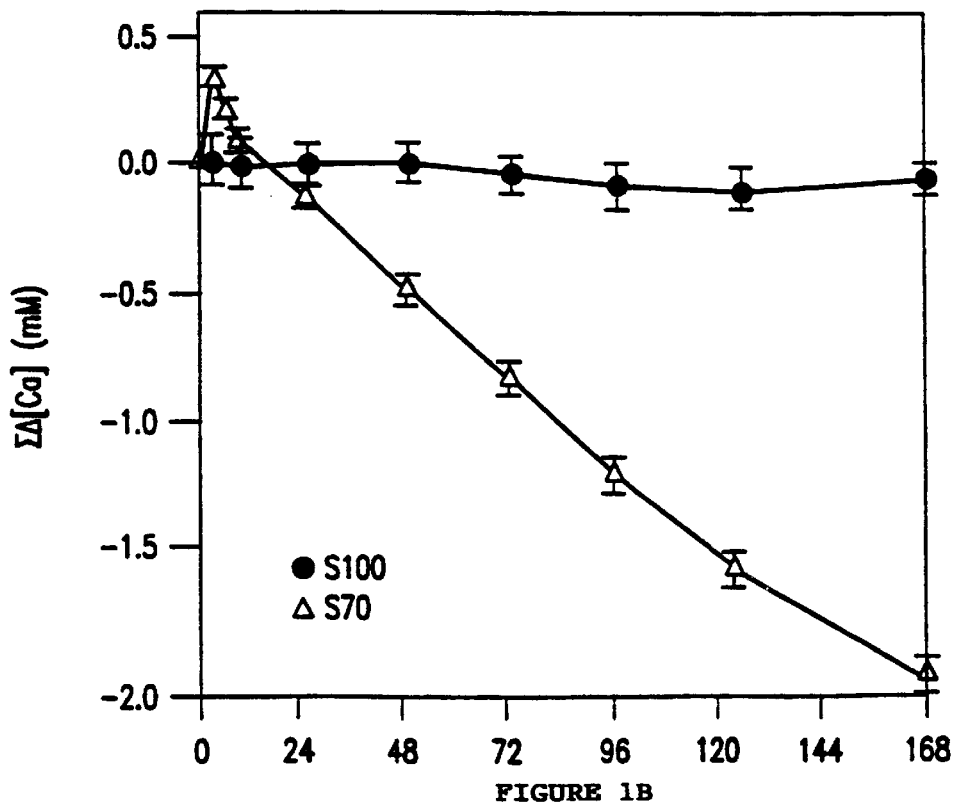
Figure 1C:
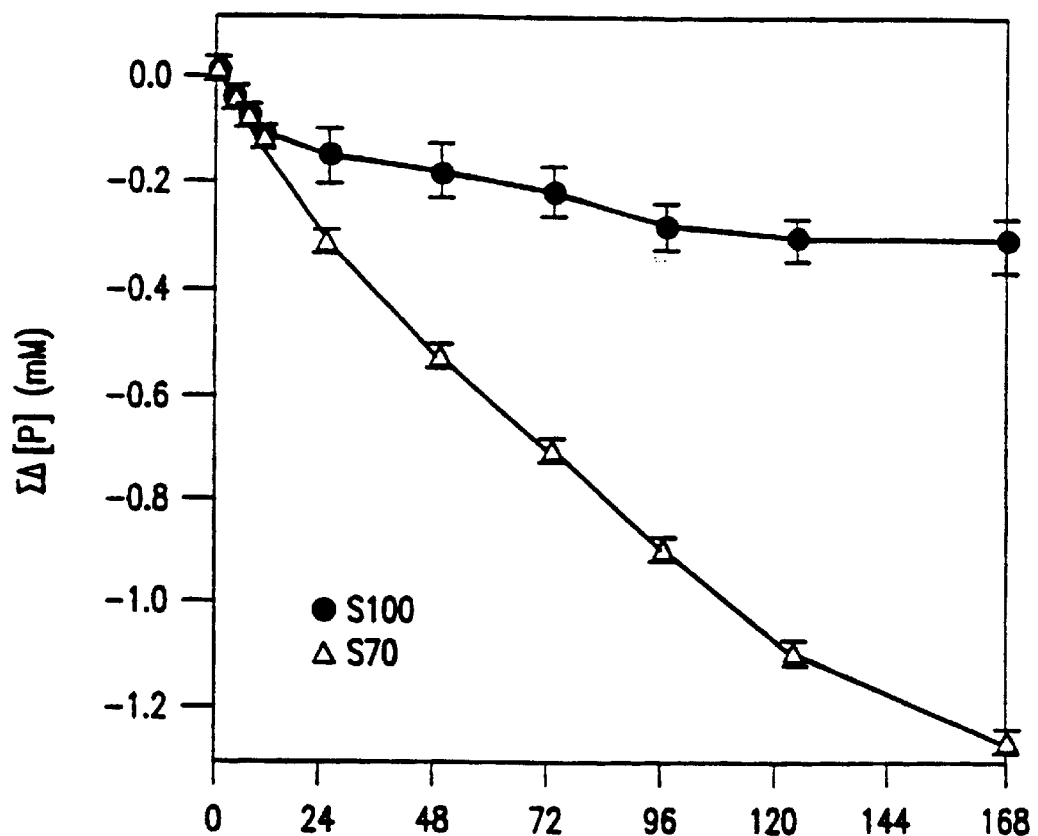

The cumulative variation of the Si, Ca, and P concentration in TE as a function of time of immersion is shown in FIGS. 1a–c. The error bars represent the standard deviation of the means. As is evident from FIG. 2a, 80% of the initial silicon content is released from the S70 glass after 48 hours of immersion and no silicon remained after a 7-day period. FIGS. 1b and 1c show that the Si dissolution from S70 is accompanied by the formation of a Ca-P phase, as indicated by a continuous calcium and phosphate uptake from solution. For S100 glass, 60% of the initial silicon was released after 72 hours and, again, no silicon remained after a 7-day period. However, Si dissolution from S100 was not accompanied by a formation of a Ca-P phase, as indicated by the lack of uptake of calcium and phosphate from solution. The presence of Vancomycin in S100 did not affect the dissolution behavior of the composite, as indicated by the similar release profiles.

To determine the immersion-induced compositional and structural changes, the reacted particles were analyzed with the same techniques as used for the characterization. In addition, scanning electron microscopy in combination with energy dispersive x-ray analysis (SEM-EDXA, JEOL T300A) was employed.

FTIR analysis confirmed the formation of a calcium-phosphate material with the characteristics of a crystalline, carbonated hydroxyapatite similar to bone-mineral Ca-P.

Figure 2:
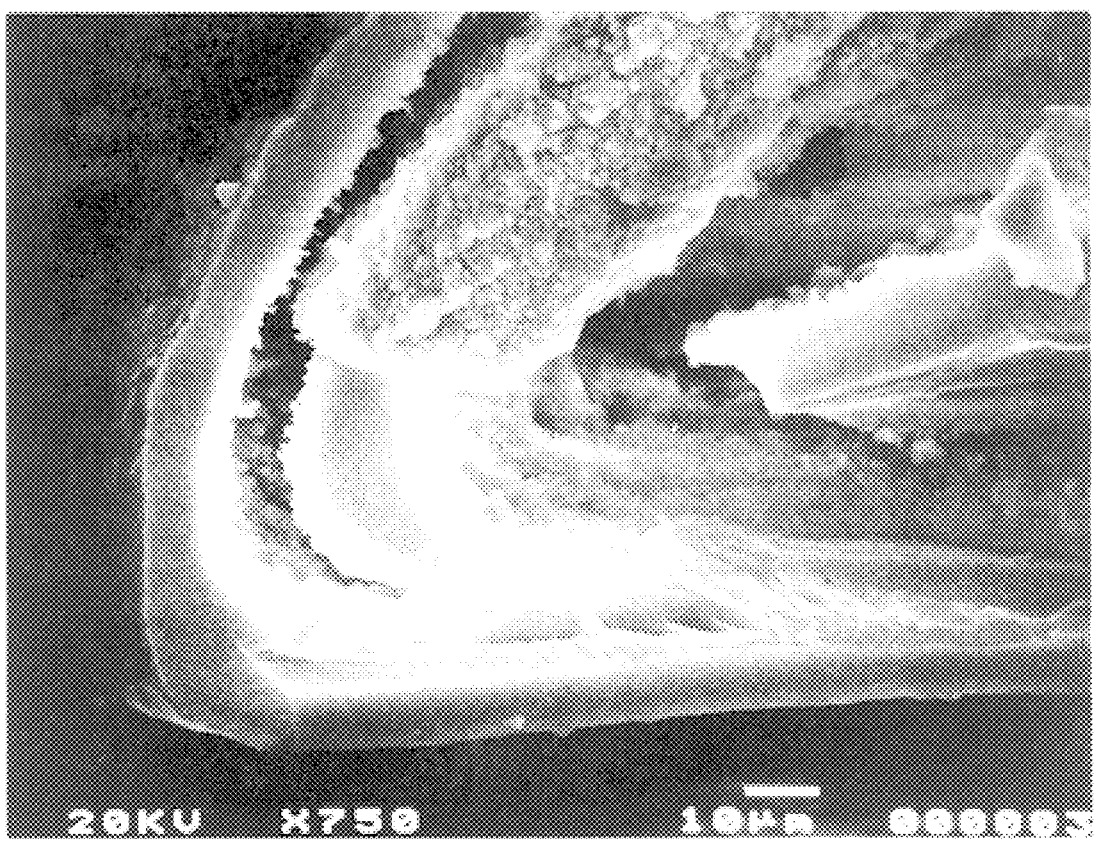
FIG. 2 is a Scanning Electron Micrograph depicting a hollow calcium-phosphate particle formed from sol-gel derived glass.

SEM micrographs of S70 reacted particles show that the particles are transformed into Ca and P containing shells (see FIG. 2, X 750). The sample was prepared for SEM examination by fracturing it. As a result, the interior of the particle was exposed. The SEM examination revealed that the particle had been transformed into a shell by the immersion treatment.

EDXA analysis only detected calcium and phosphorus, but no silicon. The Ca/P ratio of the shell as measured by EDXA is 1.5. The shell was approximately 10 μm thick.

Figure 3:
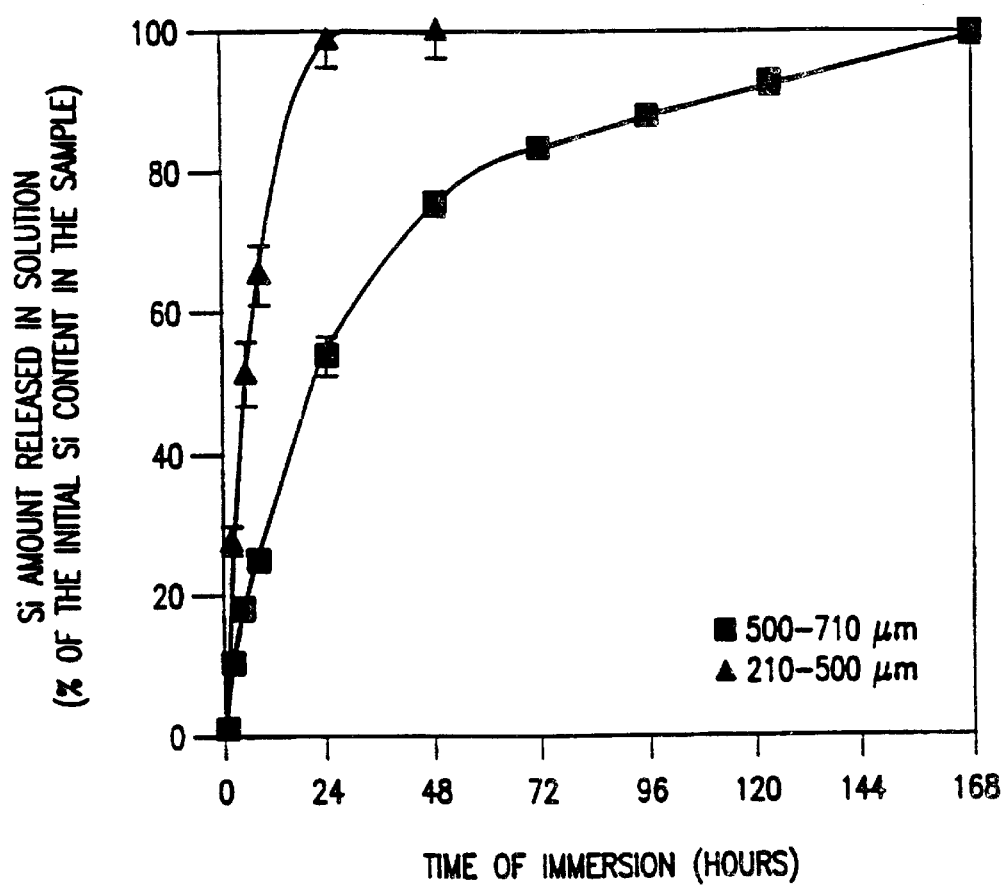
FIG. 3 depicts changes in Si content during immersion of sol-gel derived particles of S70 glass composition as a function of particle size.

FIG. 3 shows the silicon release profile S70 particles of two sizes ranges. These results indicate that the dissolution rate increases with decreasing particle size or increasing external surface area. Moreover, the S70 particles of the smaller size range exhibit the same transformation into shell-like shape as found for the larger particles.

Figure 4:
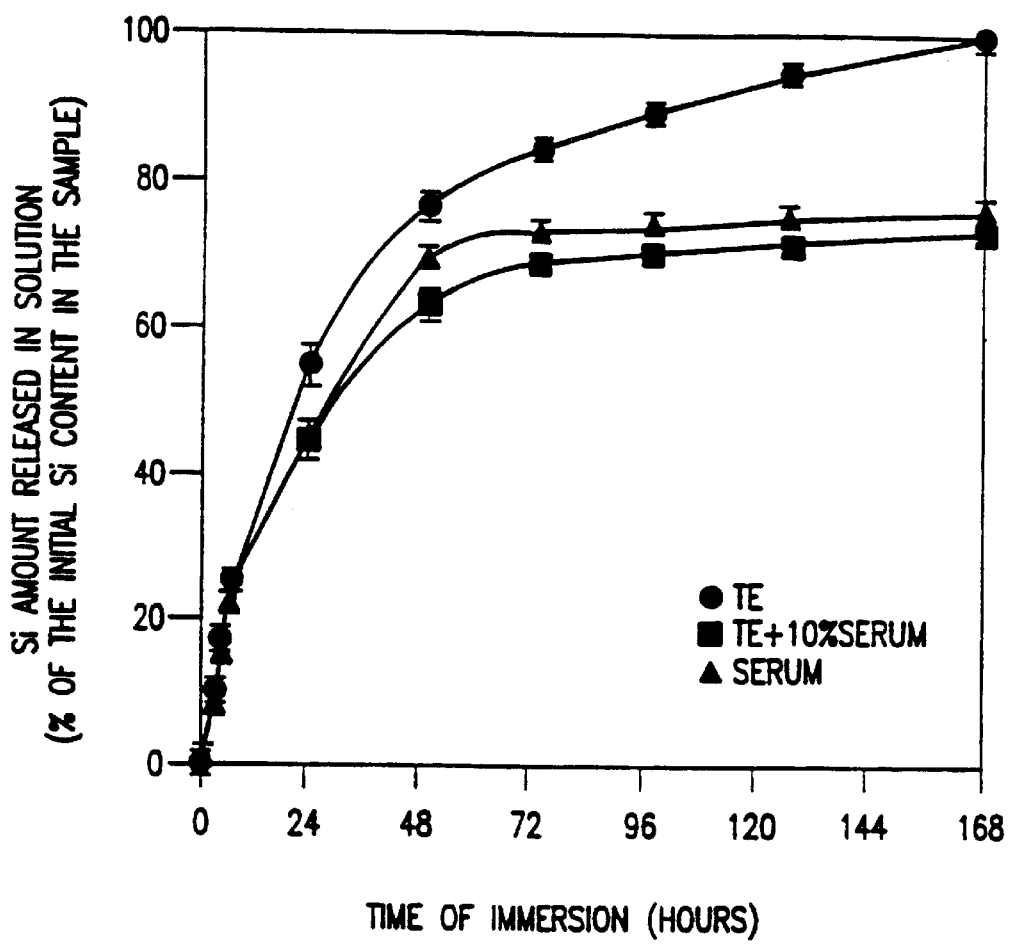
FIG. 4 depicts the effect of serum on amount of Si released for S70 sol-gel derived glass particles.

FIG. 4 shows the dissolution behavior of S70 in TE, TE supplemented with 10% serum, and serum. The presence of serum in the immersion solution decreased the rate of dissolution. Statistical analysis revealed that the release profiles differed significantly among solutions ($p<0.05$, analysis of variance) except for TE supplemented with 10% serum and 100% serum.

EXAMPLE 2
Conditioning of bioactive glass surfaces
A) Modification of melt-derived glass 45S5 granules by differential immersion in serum-containing solution Surface modification of melt-derived bioactive glass 45S5 granules having a size of about 300 to about 355 μm as obtained by sieving was conducted by differential immersion in Tris buffered (pH 7.4 at 37° C.) solution supplemented by electrolytes typical for plasma (Table I) and 10% newborn bovine serum (TES) for up to 1 week. The samples were immersed at 1 mg/ml weight-to-solution (W/V) ratio. The solution was exchanged at 3, 12, 24, 48, 96 and 168 hours. The post-immersion samples were dried and proceeded for the surface analysis.

Figure 5A:
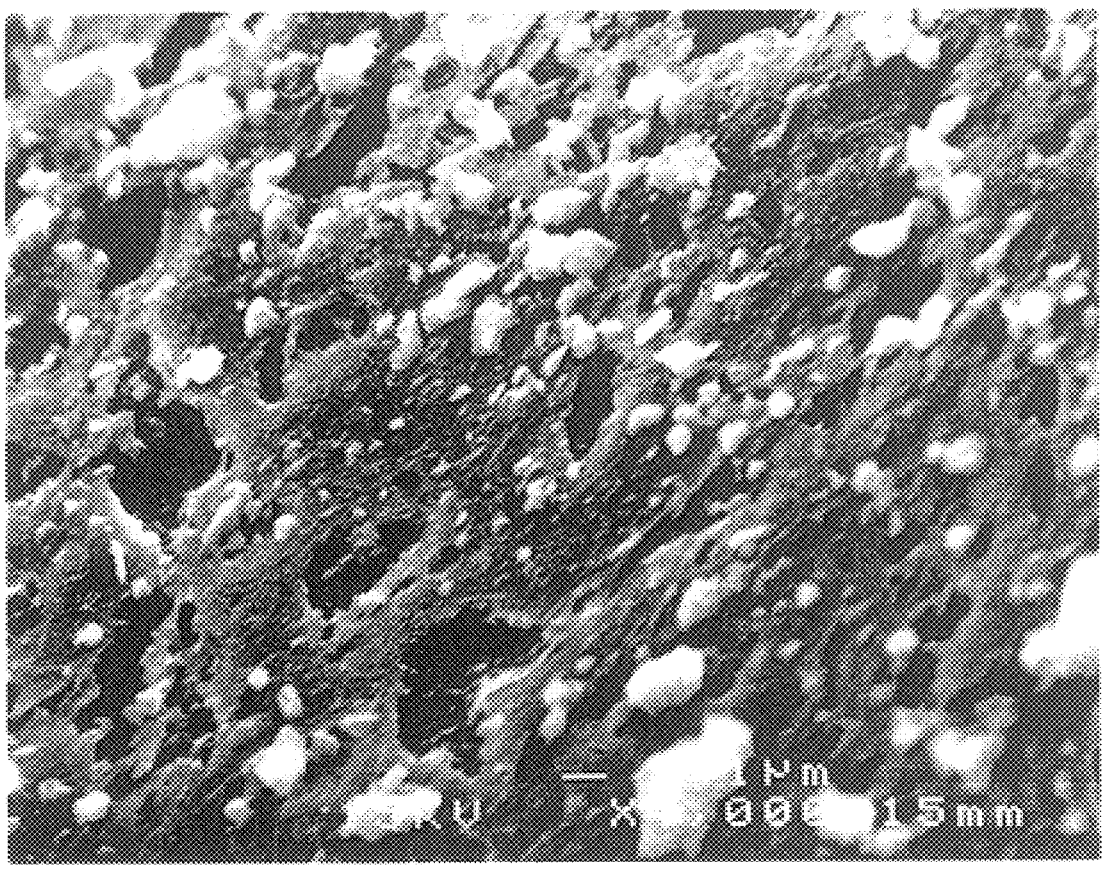
FIGS. 5a–c are SEM, EDXA, and FTIR, respectively, depicting the changes in morphology, composition and structure, respectively, of the surfaces following differential immersion in serum-containing solution.

Morphology, composition and structure of the surfaces, modified by differential immersion in serum-containing solution, are shown on the SEM micrograph and corresponding EDXA and FTIR spectra (FIGS. 5 a–c).

Figure 5B:
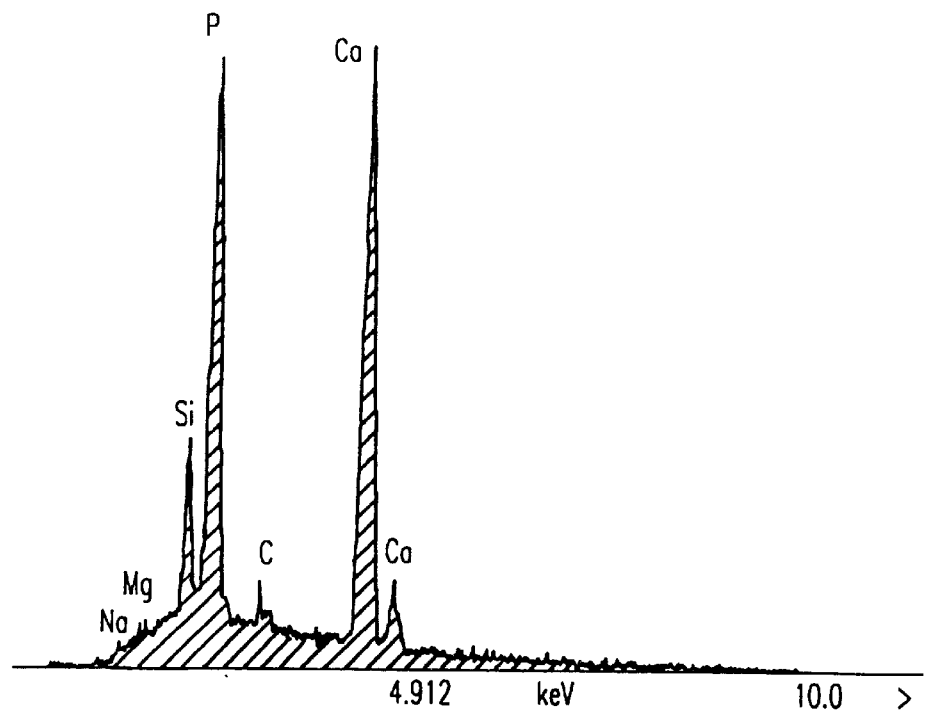
Figure 5C:
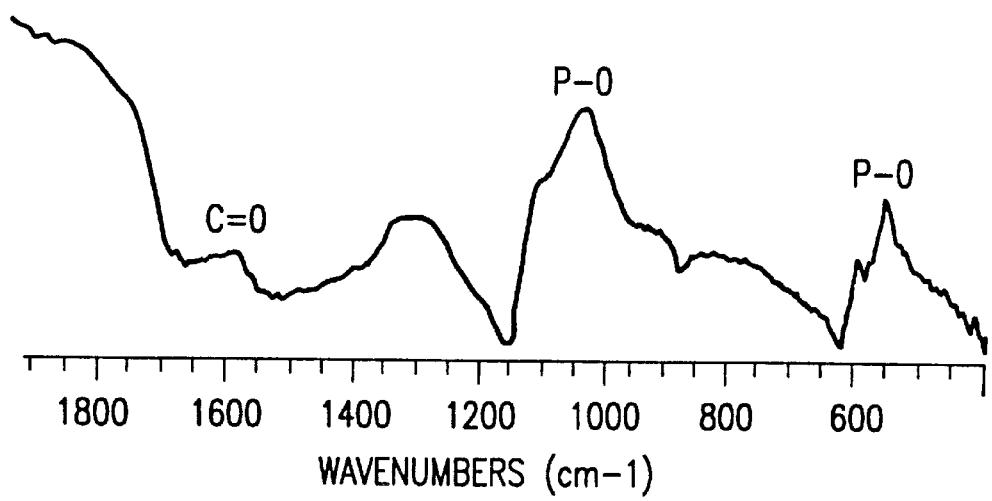

SEM micrograph (FIG. 5a) of the surface indicates that differential immersion in serum-containing solution led to formation of a microporous surface on top of dense glass. The surface layer comprises very fine (0.2 to 1 μm) precipitates. The pore size varies from 0.5 to 3 μm. The surface was mainly composed of Ca-P phases with addition of Si (FIG. 5b). The presence of the Ca-P phases is confirmed by FTIR analysis (FIG. 5c). Split of the P-O bands, recorded on the FTIR spectrum, suggests that the Ca-P phases were crystalline. The appearance of the C=O band indicates the presence of adsorbed proteins in the surface layer.

Figure 6A:
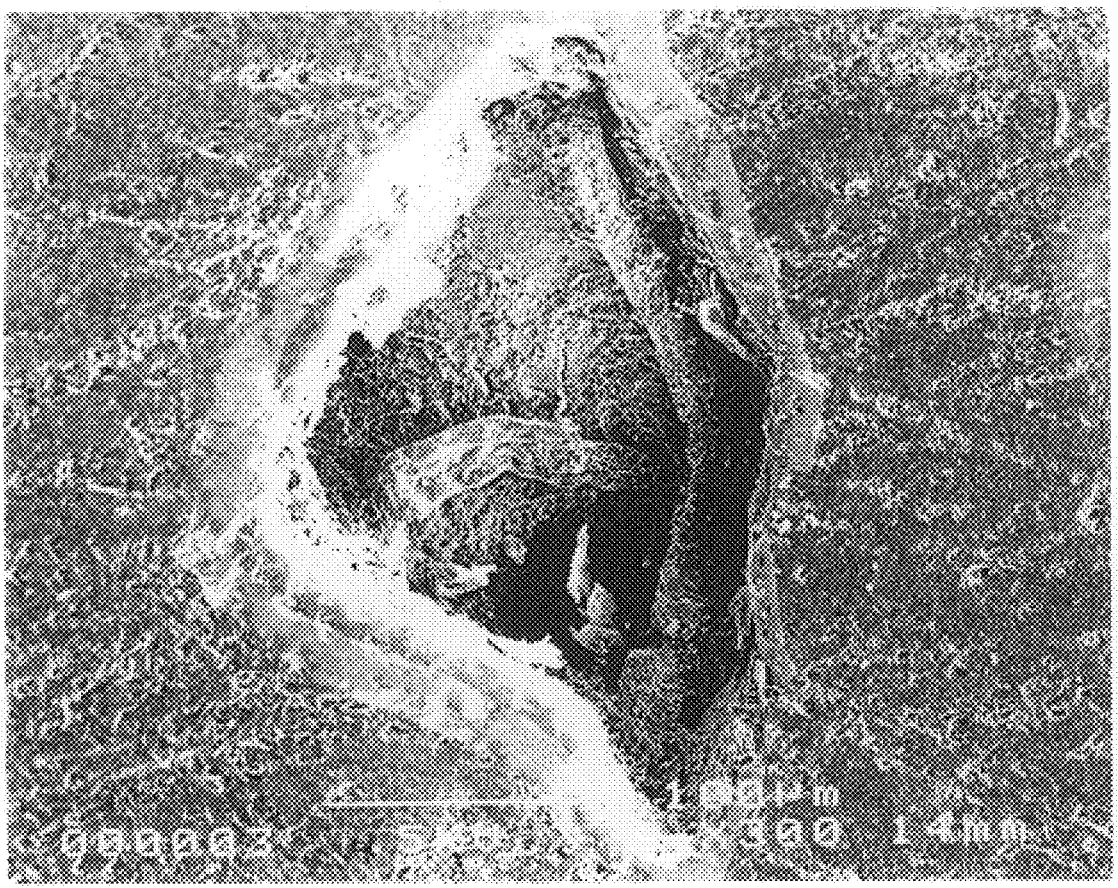
FIGS. 6a–c are SEM, EDXA, and extended carbon peaks of a cross-section of a granule following differential immersion in serum-containing solution.
Figure 6B:
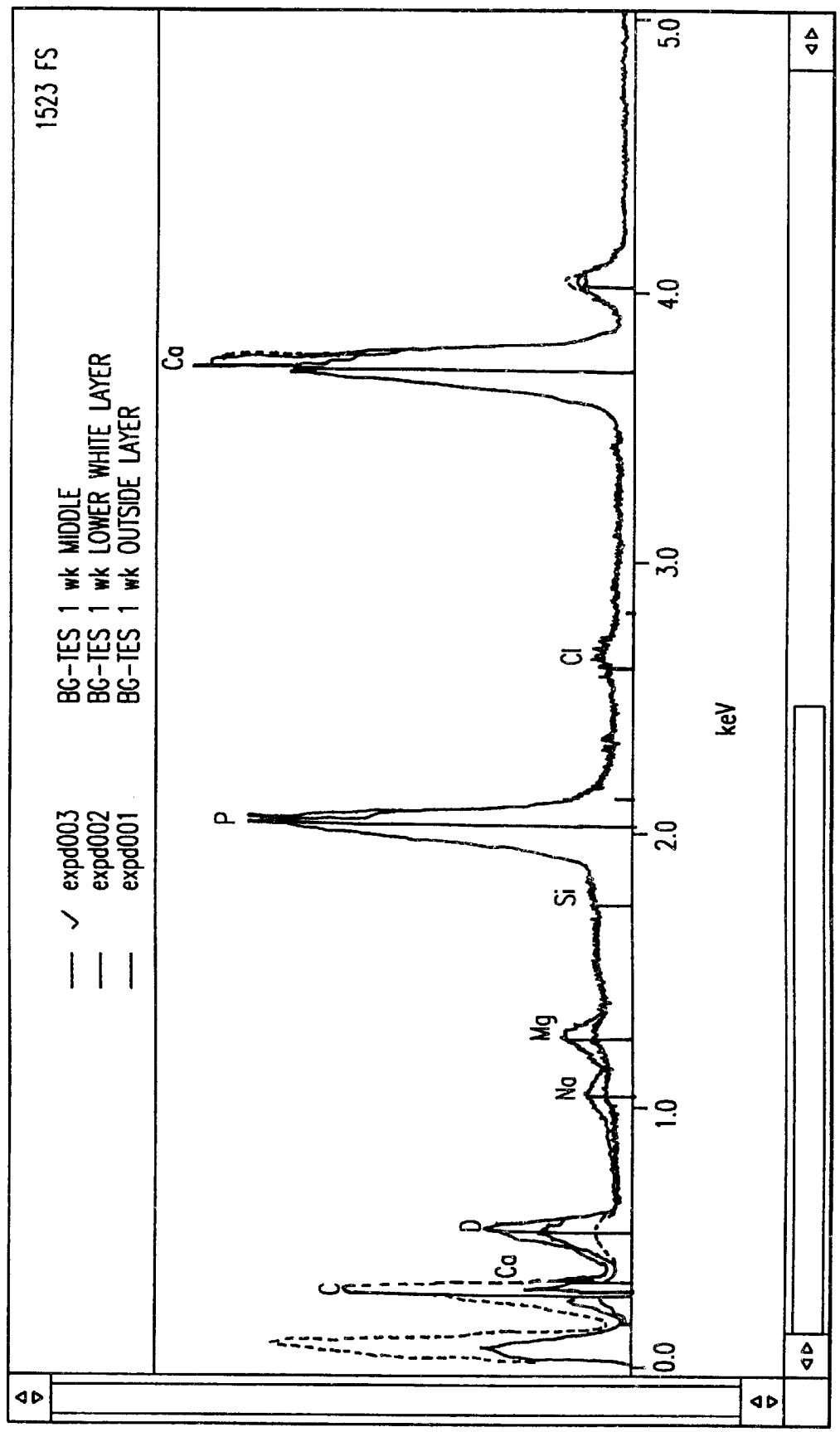
Figure 6C:
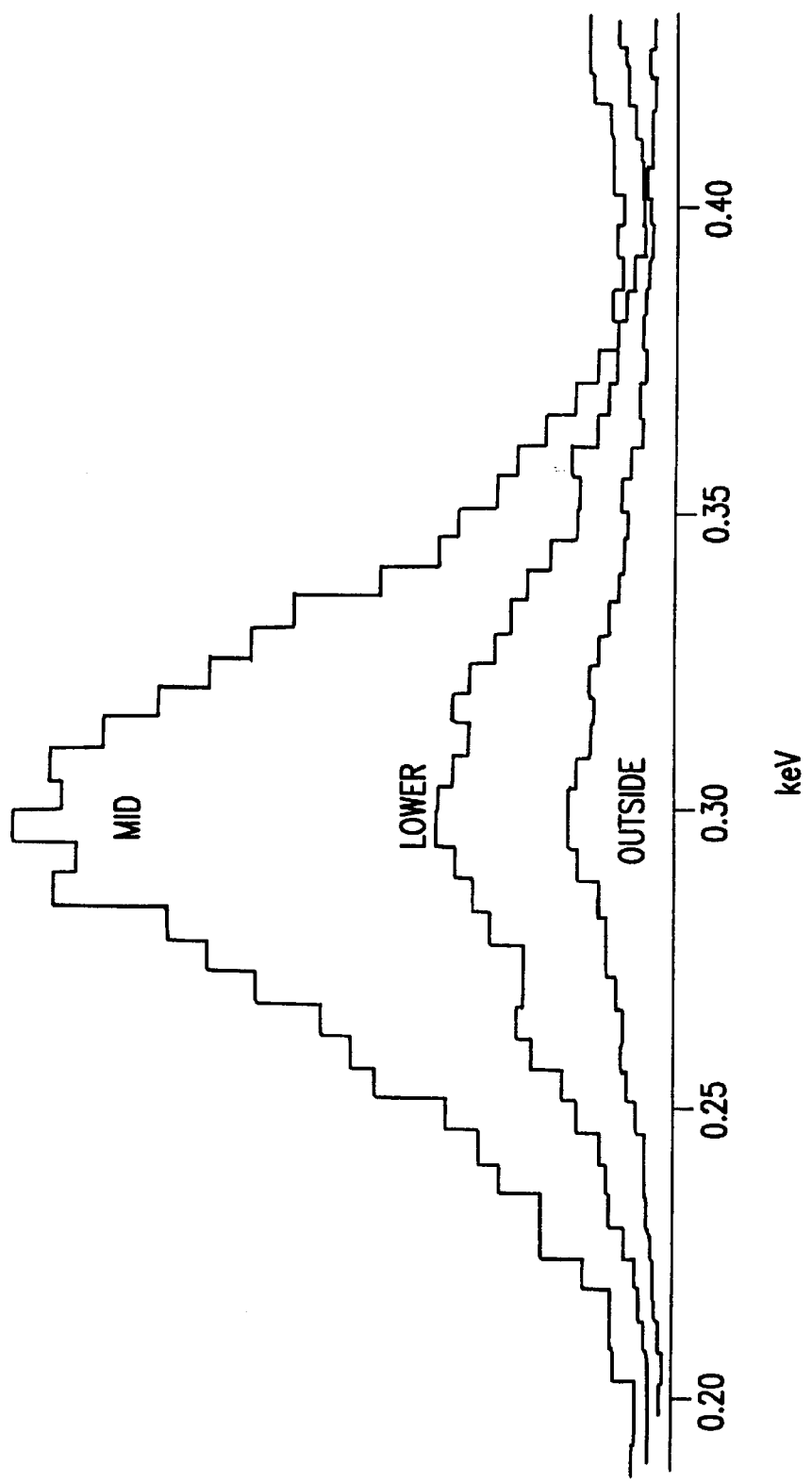

FIGS. 6 a–c depict an SEM of a cross-section of a granule treated by differential immersion as described above (FIG. 6a), full EDXA spectra of the cross-section (FIG. 6b), and extended carbon peaks from the EDXA spectra. The EDXA spectra were taken in three spots located either on the outer side (O), in the middle of (M), or on the lower side, i.e., inner side, (L), of the granule. As is clear from these spectra, carbon is present throughout the particle. These results indicate that the serum proteins are present throughout the Ca-P layer, which is 25–30 microns thick in FIG. 6a.

B) Modification of melt-derived glass 45S5 granules by differential immersion in serum-free solution Bioactive glass samples as described in A) were immersed differentially in serum-free Tris buffered solution complemented by electrolytes typical for plasma (TE) for up to 1 week. The samples were immersed at 1 mg/ml W/V ratio. The solution was exchanged at 3, 12, 24, 48, 96 and 168 hours. The post-immersion samples were dried and proceeded for the surface analysis.

Morphology, composition and structure of the immersion-modified surface are shown on FIGS. 7 a–c.

SEM micrograph (FIG. 7a) shows the appearance of the reaction surface layer (central and left parts of the picture) on top of the fractured sample. The layer appears as dense and composed of closely packed globular precipitates. The EDXA (FIG. 7b) indicates that the precipitates comprise Ca-P phases. No significant Si-content was detected in the surface layer. Split of the P-O bands, recorded on the FTIR spectrum (FIG. 7c), suggests that the Ca-P phases were crystalline.

C) Modification of melt-derived glass 45S5 granules by integral immersion in serum-free solution followed by immersion in serum-containing solution Bioactive glass samples as described in A) were immersed integrally (no solution exchange) in serum-free Tris buffered solution complemented with electrolytes typical for plasma (TE) for 48 hours and then re-immersed in serum-containing TES for either 1, 3 or 6 hours. After immersion the samples were dried and proceeded for surface analysis.

Figure 8A:
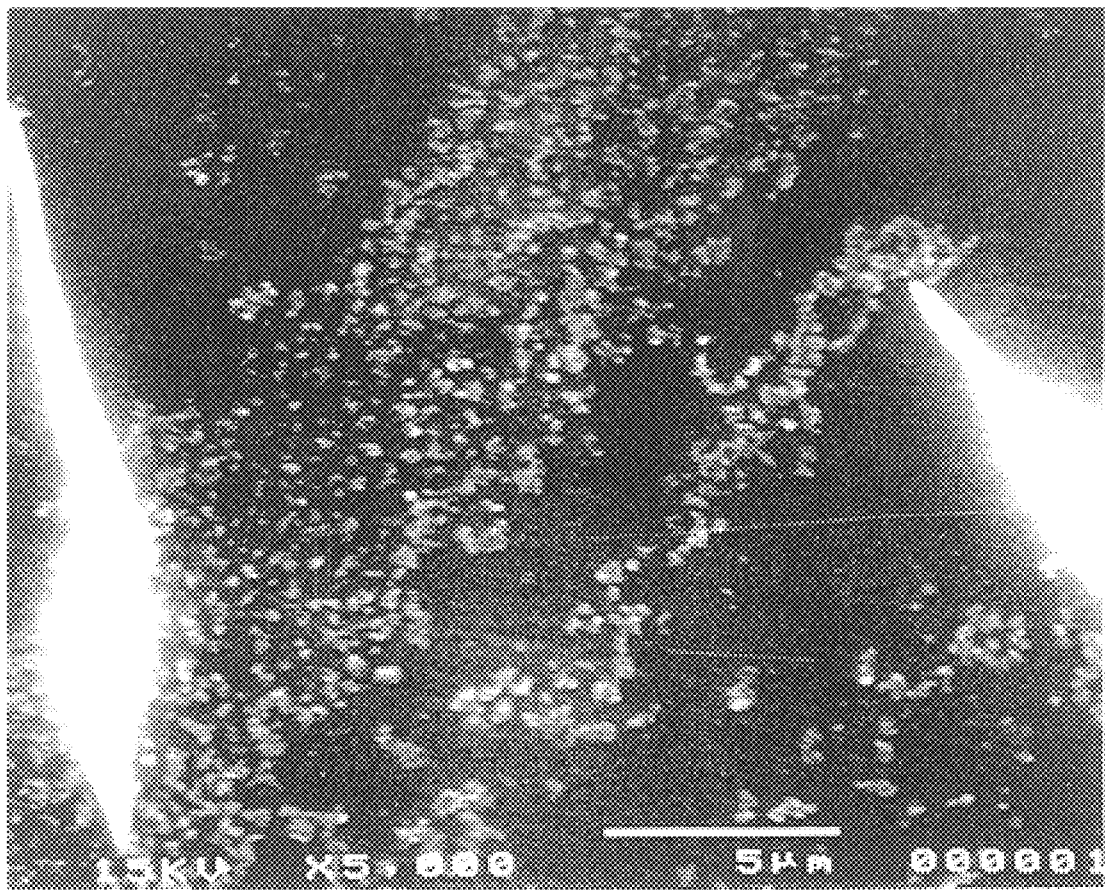
FIGS. 8a–c are SEM, EDXA, and FTIR, respectively, depicting the changes in morphology, composition, and structure, respectively, of the surfaces following integral immersion in serum-free solution followed by immersion in serum-containing solution.
Figure 8B:
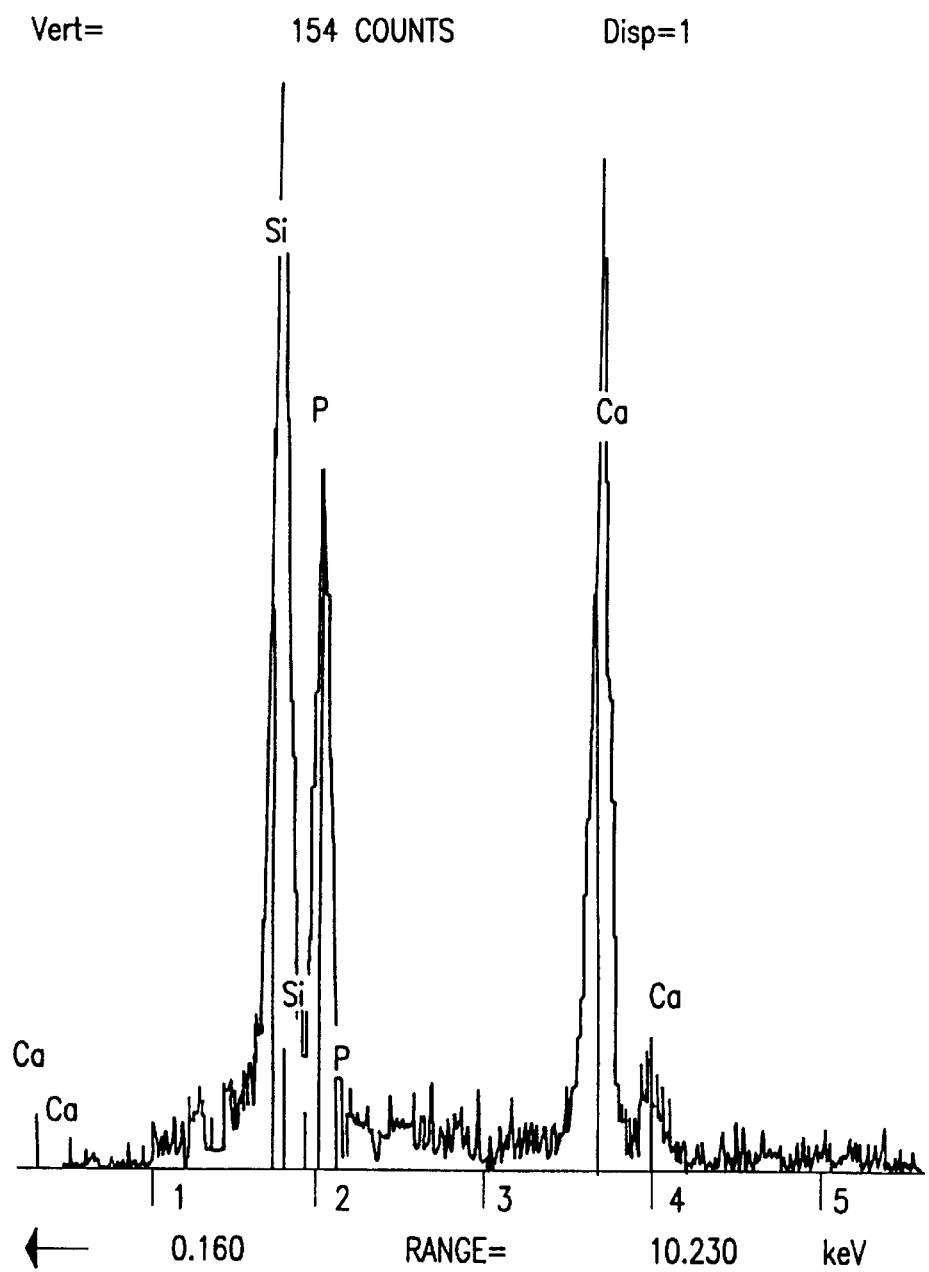
Figure 8C:
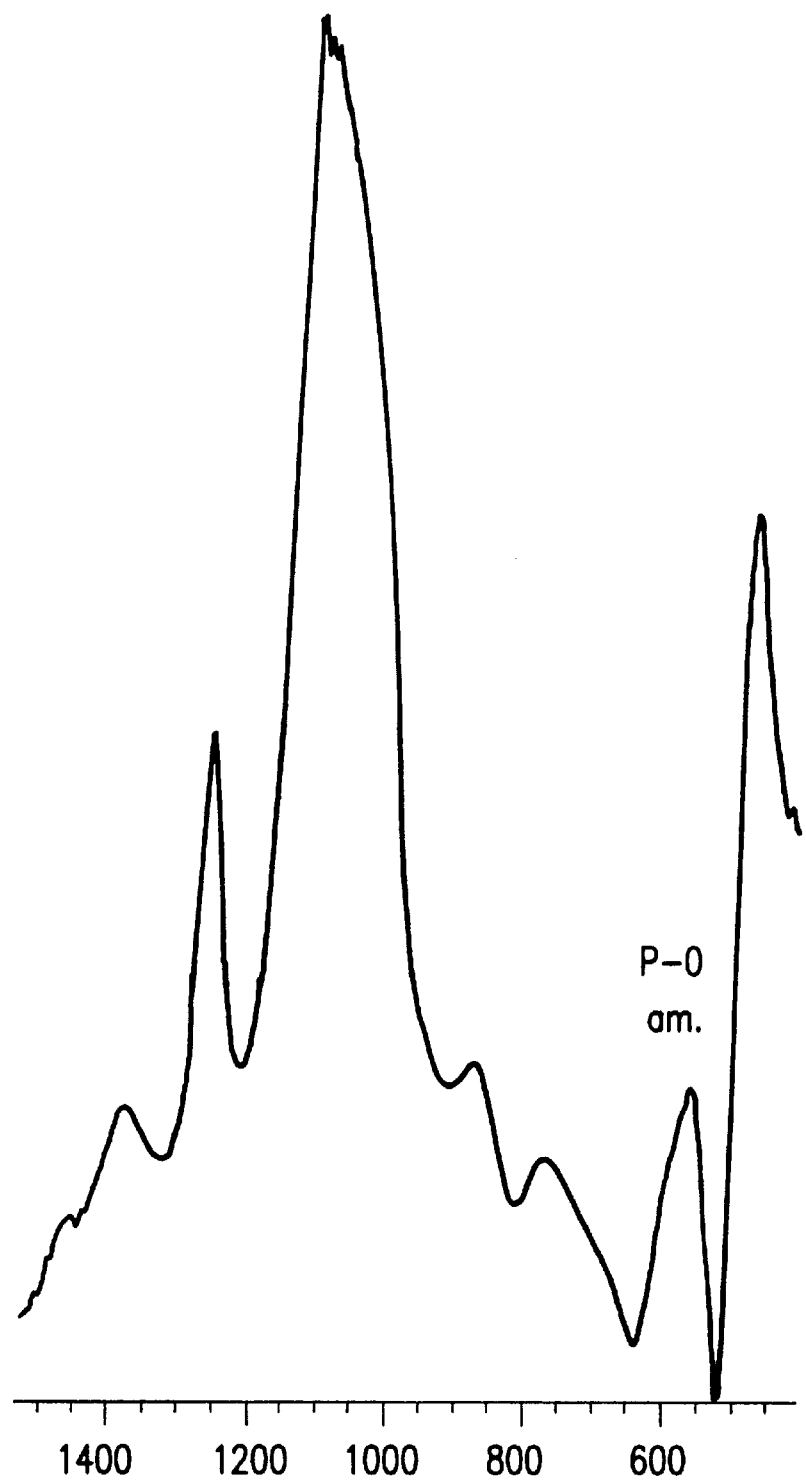

Morphology, composition and structure of the bioactive glass surface after immersion in TE for 48 hours and subsequent immersion in TES for 1 hour are shown on FIGS. 8 a–c. Extension of immersion in TES for up to 6 hours did not produce a significant change in the surface morphology and composition.

SEM micrograph (FIG. 8a) indicates that the reaction surface appears as a smooth, dense layer with patchy globular precipitates (cracks are artifacts due to drying). EDXA reveals that the surface layer has a major Si-content with addition of Ca and P (FIG. 8b). The appearance of an undivided P-O band on the FTIR spectrum suggests the Ca-P phases were amorphous.

The smooth reaction layer is composed of silica-matrix with Ca-P accumulations in it. Subsequent to formation of this layer Ca-P precipitation occurs on top of it.

Figure 9:
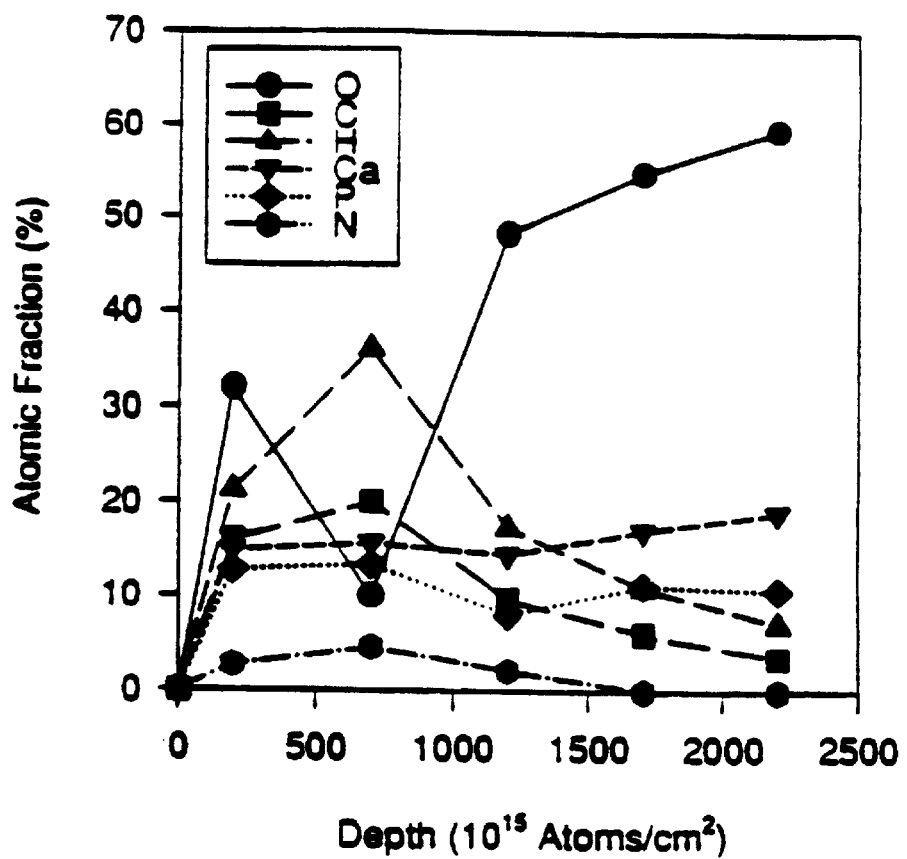
FIG. 9 is an RBS of a sample following integral immersion in serum-free solution followed by immersion in serum-containing solution.

A Rutherford backscattering spectrum (RBS) of a bioactive glass disk immersed as described above (i.e., integrally for 48 hours in TE followed by immersion in tissue culture medium containing 10% NU serum for one hour) is depicted in FIG. 9. The sample was washed after immersion by using ethanol and acetone, and then air dried. The depth profile for carbon and nitrogen showed the adsorption of about 1000 monolayers of proteinaceous material onto the Ca-P layer. The surface resolution of RBS is very high. Accordingly, probing depth is typically limited to about 0.1 to 1 micrometer. The results indicate, therefore, that the proteinaceous material is concentrated at the surface after such treatment and not throughout the Ca-P layer.

D) Modification of melt-derived glass 45S5 granules by integral immersion in serum-containing solution Bioactive glass samples as described in A) were immersed integrally (no solution exchange) in serum-containing TES for 1 week. After immersion the samples were dried and proceeded for the surface analysis.

Morphology, composition and structure of the immersion-modified surface are shown on FIGS. 10 a–d.

SEM micrograph (FIG. 10a) shows that the reaction surface appears as a smooth and dense layer (cracks are artifacts due to drying). No precipitation was observed on top of this layer. EDXA spectrum on FIG. 10b indicates that the layer has a major Si-content (50%, atomic) with addition of Ca and P. The underlying layer, exposed in cracks, is mainly composed of silica (FIG. 10c). The appearance of an undivided P-O band on the FTIR spectrum (FIG. 10d) indicates that the Ca-P phases were amorphous.

The smooth reaction layers, formed on top of bioactive glass 45S5, are composed of silica-matrix with amorphous Ca-P accumulations in it.

The foregoing examples are meant to illustrate the invention and not to limit it in any way. Those skilled in the art will recognize that modifications can be made which are within the spirit and scope of the invention as set forth in the appended claims.

All references cited herein are hereby incorporated by reference in their entirety.

What is claimed is:

1. A method for conditioning the surface of silica-based glass or ceramic containing calcium and phosphate comprising:

a) immersing said glass or ceramic in an aqueous solution containing serum-protein like organic molecules for a period of time sufficient to form a microporous calcium-phosphate (Ca-P) surface layer having serum-protein like organic molecules intermingled throughout; and b) exchanging by continuous flow of solution the solution during said period of time at intervals sufficient to allow continuous formation of the microporous Ca-P layer;

wherein the concentration of said serum in said aqueous solution is from about 1% to about 100%.

2. The method according to claim 1 wherein said glass or ceramic is macroporous.

3. The method according to claim 1 wherein said glass or ceramic is dense.

4. The method according to claim 1 further comprising c) immersing said conditioned glass or ceramic in a second aqueous solution comprising biologically active molecules.

5. The method according to claim 1 wherein said period of time is up to about two weeks.

6. A method for conditioning the surface of silica-based glass or ceramic containing calcium and phosphate comprising:

a) immersing said glass or ceramic in an aqueous solution containing serum-protein like organic molecules for a period of time sufficient to form a microporous calcium-phosphate (Ca-P) surface layer having serum-protein like organic molecules intermingled throughout; and b) exchanging by total solution exchange the solution during said period of time at intervals sufficient to allow continuous formation of the microporous Ca-P layer;

wherein the concentration of said serum in said aqueous solution is from about 1% to about 100%.

7. The method according to claim 6 wherein said period of time is up to about two weeks.

8. The method according to claim 1 wherein the concentration of said serum in said aqueous solution is from about 8% to about 100%.

9. The method according to claim 1 wherein said glass or ceramic is macroporous.

10. The method according to claim 1 wherein said glass or ceramic is dense.

11. The method according to claim 1 further comprising c) immersing said conditioned glass or ceramic in a second aqueous solution comprising biologically active molecules.

12. The method according to claim 1 or 11 wherein said aqueous solution of steps a) and b) further comprises biologically active molecules.

13. The method according to claim 1 wherein said microporous Ca-P surface layer further comprises silicon.

14. The method according to claim 6 wherein the concentration of said serum in said aqueous solution is from about 8% to about 100%.

15. The method according to claim 6 or 4 wherein said aqueous solution of steps a) and b) further comprises biologically active molecules.

16. The method according to claim 6 wherein said microporous Ca-P surface layer further comprises silicon.

* * * * *

UNITED STATES PATENT AND TRADEMARK OFFICE
CERTIFICATE OF CORRECTION

PATENT NO. : 6,569,466 B2
DATED : May 27, 2003
INVENTOR(S) : Paul Ducheyne et al.

It is certified that error appears in the above-identified patent and that said Letters Patent is hereby corrected as shown below:

Column 1,
Line 65, delete the word "in vivo" and insert therefore -- *in vivo* --

Column 2,
Line 13, delete the word "in vitro" and insert therefore -- *in vitro* --
Line 14, delete the word "in vivo" and insert therefore -- *in vivo* --

Column 3,
Lines 18, 19, 23 and 65, delete the word "in vitro" and insert therefore -- *in vitro* --
Line 19, delete the word "in" following the word "or" and insert therefore -- *in-* --
Line 20, delete the word "vivo" and insert therefore -- *vivo* --
Line 29, delete the words "in vitro or in vivo" and insert therefore
-- *in vitro or in vivo* --; and
Line 36, following "400º C" and before "were", delete "."

Column 4,
Line 2, delete the word "inter alia" and insert therefore -- *inter alia* --; and
Line 23, delete the word "in vitro" and insert therefore -- *in vitro* --

Column 5,
Line 20, delete the word "define" and insert therefore -- defined --
Line 26, delete the word "supra" and insert therefore -- *supra* --
Line 46, delete the word "in vitro" and insert therefore -- *in vitro* --
Line 48, delete the word "in vivo" and insert therefore -- *in vivo* --

Signed and Sealed this

Twenty-second Day of July, 2003

JAMES E. ROGAN
*Director of the United States Patent and Trademark Office*